(12) United States Patent
Tinjust

(10) Patent No.: US 10,478,698 B2
(45) Date of Patent: Nov. 19, 2019

(54) INTERACTIVE COGNITIVE-MULTISENSORY INTERFACE APPARATUS AND METHODS FOR ASSESSING, PROFILING, TRAINING, AND/OR IMPROVING PERFORMANCE OF ATHLETES AND OTHER POPULATIONS

(71) Applicant: APEXK INC., Laval (CA)

(72) Inventor: David Tinjust, Ville St-Laurent (CA)

(73) Assignee: APEXK INC., Laval, QC (CA)

( * ) Notice: Subject to any disclaimer, the term of this patent is extended or adjusted under 35 U.S.C. 154(b) by 1227 days.

(21) Appl. No.: 14/391,063

(22) PCT Filed: Apr. 9, 2013

(86) PCT No.: PCT/CA2013/050281
§ 371 (c)(1),
(2) Date: Oct. 7, 2014

(87) PCT Pub. No.: WO2013/152443
PCT Pub. Date: Oct. 17, 2013

(65) Prior Publication Data
US 2015/0140529 A1 May 21, 2015

Related U.S. Application Data

(63) Continuation of application No. 13/443,380, filed on Apr. 10, 2012, now Pat. No. 9,248,358.
(Continued)

(51) Int. Cl.
*A61B 5/16* (2006.01)
*A63B 69/00* (2006.01)
(Continued)

(52) U.S. Cl.
CPC ............ *A63B 69/0053* (2013.01); *A61B 5/16* (2013.01); *A61B 5/742* (2013.01);
(Continued)

(58) Field of Classification Search
CPC .................................................. A63B 69/0053
(Continued)

(56) References Cited

U.S. PATENT DOCUMENTS

| 4,166,452 A | 9/1979 | Generales, Jr. |
| 4,199,987 A | 4/1980 | Bauers et al. |

(Continued)

FOREIGN PATENT DOCUMENTS

| CN | 102333574 A | 1/2012 |
| EP | 0251541 A2 | 1/1988 |

(Continued)

OTHER PUBLICATIONS

EP application 13775385.1 search opinion dated Dec. 14, 2015.
(Continued)

*Primary Examiner* — Samchuan C Yao
*Assistant Examiner* — Jennifer L Korb
(74) *Attorney, Agent, or Firm* — Anglehart et al.

(57) ABSTRACT

A cognitive/multisensory stimulation system simulates sports scenarios during real sports actions for assessing, profiling, training, or improving performance of athletes or other populations. Cognitive/multisensory training can be provided by: establishing with an athlete a sensory semantic language for relating a number of sensory signals to corresponding possible actions, the sensory semantic language being essentially new to the athlete; instructing the athlete to perform an athletic exercise involving skills and full body movement; providing during exercise sensory signals to the athlete to require rapid discernment by the athlete of the semantic meaning of the sensory signal to correctly chose one possible action; and determining whether the athlete correctly responds to the selected sensory signal during said exercise.

4 Claims, 29 Drawing Sheets

Related U.S. Application Data

(60) Provisional application No. 61/691,879, filed on Aug. 22, 2012.

(51) Int. Cl.
| | | |
|---|---|---|
| *A61B 5/00* | (2006.01) | |
| *G09B 5/02* | (2006.01) | |
| *G09B 19/00* | (2006.01) | |
| *A63B 71/06* | (2006.01) | |
| *A63B 24/00* | (2006.01) | |
| *A63B 71/00* | (2006.01) | |
| *A63B 71/02* | (2006.01) | |
| *A63B 102/24* | (2015.01) | |

(52) U.S. Cl.
CPC ...... *A63B 24/0087* (2013.01); *A63B 71/0622* (2013.01); *G09B 5/02* (2013.01); *G09B 19/0038* (2013.01); *A61B 2503/10* (2013.01); *A61B 2505/09* (2013.01); *A63B 71/0009* (2013.01); *A63B 2024/0065* (2013.01); *A63B 2024/0093* (2013.01); *A63B 2024/0096* (2013.01); *A63B 2069/0055* (2013.01); *A63B 2071/025* (2013.01); *A63B 2071/0625* (2013.01); *A63B 2071/0638* (2013.01); *A63B 2071/0655* (2013.01); *A63B 2071/0661* (2013.01); *A63B 2071/0666* (2013.01); *A63B 2102/24* (2015.10); *A63B 2208/14* (2013.01); *A63B 2220/801* (2013.01); *A63B 2225/10* (2013.01); *A63B 2225/15* (2013.01); *A63B 2225/50* (2013.01); *A63B 2243/007* (2013.01); *A63B 2243/0025* (2013.01); *A63B 2243/0037* (2013.01)

(58) Field of Classification Search
USPC .................................................. 434/236, 247
See application file for complete search history.

(56) References Cited

U.S. PATENT DOCUMENTS

| | | | |
|---|---|---|---|
| 4,429,961 A | 2/1984 | Sheingorn | |
| 4,534,557 A | 8/1985 | Bigelow et al. | |
| 4,627,620 A | 12/1986 | Yang | |
| 4,645,458 A | 2/1987 | Williams | |
| 4,702,475 A | 10/1987 | Elstein et al. | |
| 4,751,642 A | 6/1988 | Silva et al. | |
| 5,469,740 A | 11/1995 | French et al. | |
| 5,509,650 A | 4/1996 | MacDonald | |
| 5,584,779 A | 12/1996 | Knecht et al. | |
| 5,595,488 A | 1/1997 | Gozlan et al. | |
| 5,901,961 A | 5/1999 | Holland, III | |
| 6,066,105 A | 5/2000 | Guillen | |
| 6,430,997 B1 | 8/2002 | French et al. | |
| 6,585,622 B1 | 7/2003 | Shum et al. | |
| 6,644,976 B2 | 11/2003 | Kullok et al. | |
| 6,749,432 B2 | 6/2004 | French et al. | |
| 7,309,234 B2 | 12/2007 | Mathog | |
| 7,815,548 B2 * | 10/2010 | Barre | A63B 24/00 482/8 |
| 7,837,472 B1 | 11/2010 | Elsmore et al. | |
| 7,951,045 B1 | 5/2011 | Brader | |
| 7,959,501 B2 | 6/2011 | Harmon et al. | |
| 8,043,173 B2 | 10/2011 | Menalagha et al. | |
| 8,113,991 B2 | 2/2012 | Kutliroff | |
| 8,342,968 B2 | 1/2013 | Fuccillo et al. | |
| 2004/0072133 A1 | 4/2004 | Kullok et al. | |
| 2005/0021110 A1 | 1/2005 | Maschke et al. | |
| 2005/0165327 A1 * | 7/2005 | Thibault | A61B 3/0066 600/558 |
| 2006/0281061 A1 | 12/2006 | Hightower et al. | |
| 2007/0213126 A1 * | 9/2007 | Deutsch | G07C 1/22 463/36 |
| 2008/0032271 A1 | 2/2008 | Johnson | |
| 2009/0281450 A1 | 11/2009 | Reichow et al. | |
| 2009/0312817 A1 | 12/2009 | Hogle et al. | |
| 2010/0112533 A1 | 5/2010 | Chan et al. | |
| 2010/0129780 A1 | 5/2010 | Homsi et al. | |
| 2010/0255452 A1 * | 10/2010 | Coffey | G09B 5/00 434/258 |
| 2011/0006926 A1 | 1/2011 | Kim et al. | |
| 2011/0112441 A1 | 5/2011 | Burdea | |
| 2011/0183783 A1 | 7/2011 | Rahim et al. | |
| 2011/0184498 A1 | 7/2011 | Donley | |
| 2011/0205167 A1 * | 8/2011 | Massengill | A61B 3/113 345/173 |
| 2011/0300522 A1 | 12/2011 | Faubert et al. | |
| 2012/0094787 A1 | 4/2012 | Weiss | |

FOREIGN PATENT DOCUMENTS

| | | |
|---|---|---|
| EP | 0587622 B2 | 3/1997 |
| GB | 2464327 A | 4/2010 |
| JP | 11-313911 A | 11/1999 |
| JP | 2007-275442 A | 10/2007 |
| KR | 2002-0022627 A | 3/2002 |
| RO | 120450 B1 | 2/2006 |
| TW | 200939137 A | 9/2009 |
| WO | WO 93/10708 A1 | 6/1993 |
| WO | WO 96/32164 A1 | 10/1996 |
| WO | WO 03/023546 A2 | 3/2003 |
| WO | WO 2007/142588 A1 | 12/2007 |
| WO | WO 2009/019638 A1 | 2/2009 |
| WO | WO 2010/037222 A1 | 4/2010 |
| WO | WO 2011/046612 A2 | 4/2011 |
| WO | WO 2011/094250 A2 | 8/2011 |
| WO | WO 2012/160368 A1 | 11/2012 |

OTHER PUBLICATIONS

EP application 13775385.1 search report dated Dec. 14, 2015 with related claims.
Poolton, JM et al, The influence of analogy learning on decision-making in table tennis: Evidence from behavioural data, Psychology of Sport and Exercise, 2006, v. 7 n. 6, p. 677-688.
PCT/CA2013/050281 international preliminary report.
PCT/CA2013/050281 international search report with claims 1-41.
CA 2869008 office action dated Dec. 4, 2015 with related claims.
CA 2984654 office action dated Jan. 2, 2019.
CN application 201380028111.7 office action dated Oct. 25, 2016.
EP application 13775385.1 office action dated Nov. 15, 2016.
U.S. Appl. No. 14/876,177 final rejection dated Apr. 2, 2018.
U.S. Appl. No. 14/876,177 first office action dated Aug. 1, 2017.
U.S. Appl. No. 14/876,177 office action dated Jul. 1, 2019.

* cited by examiner

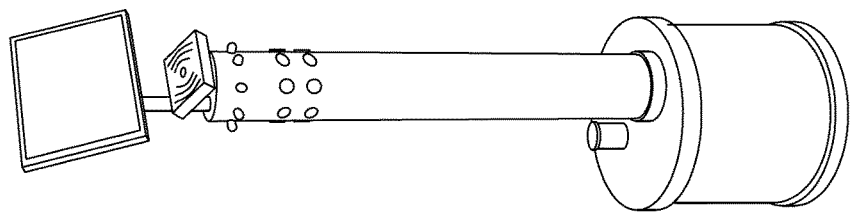
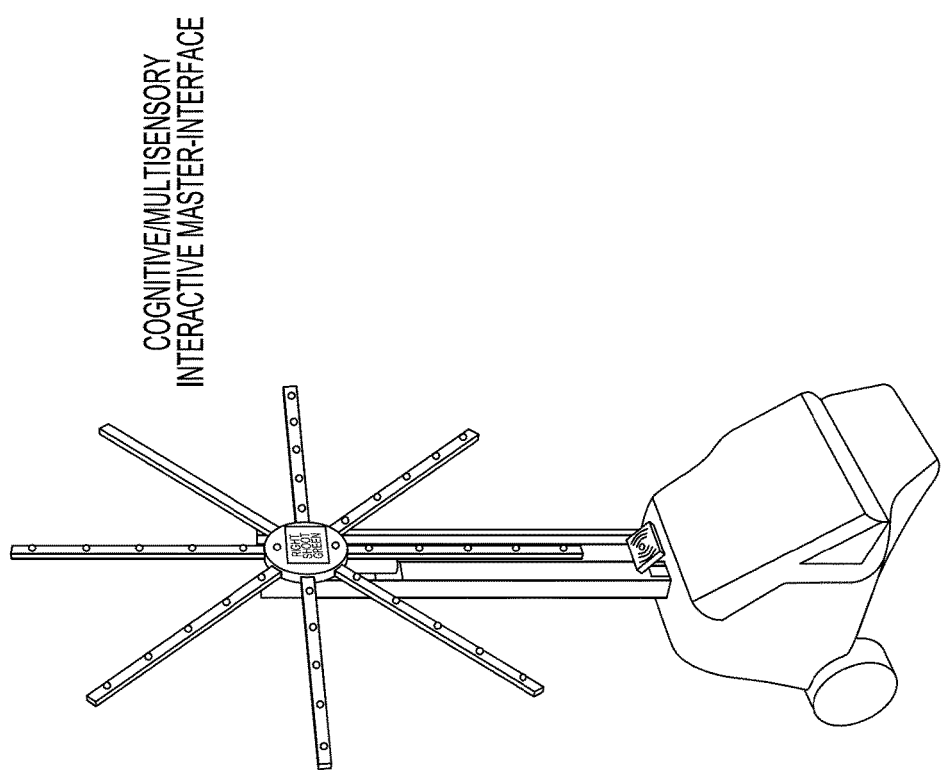

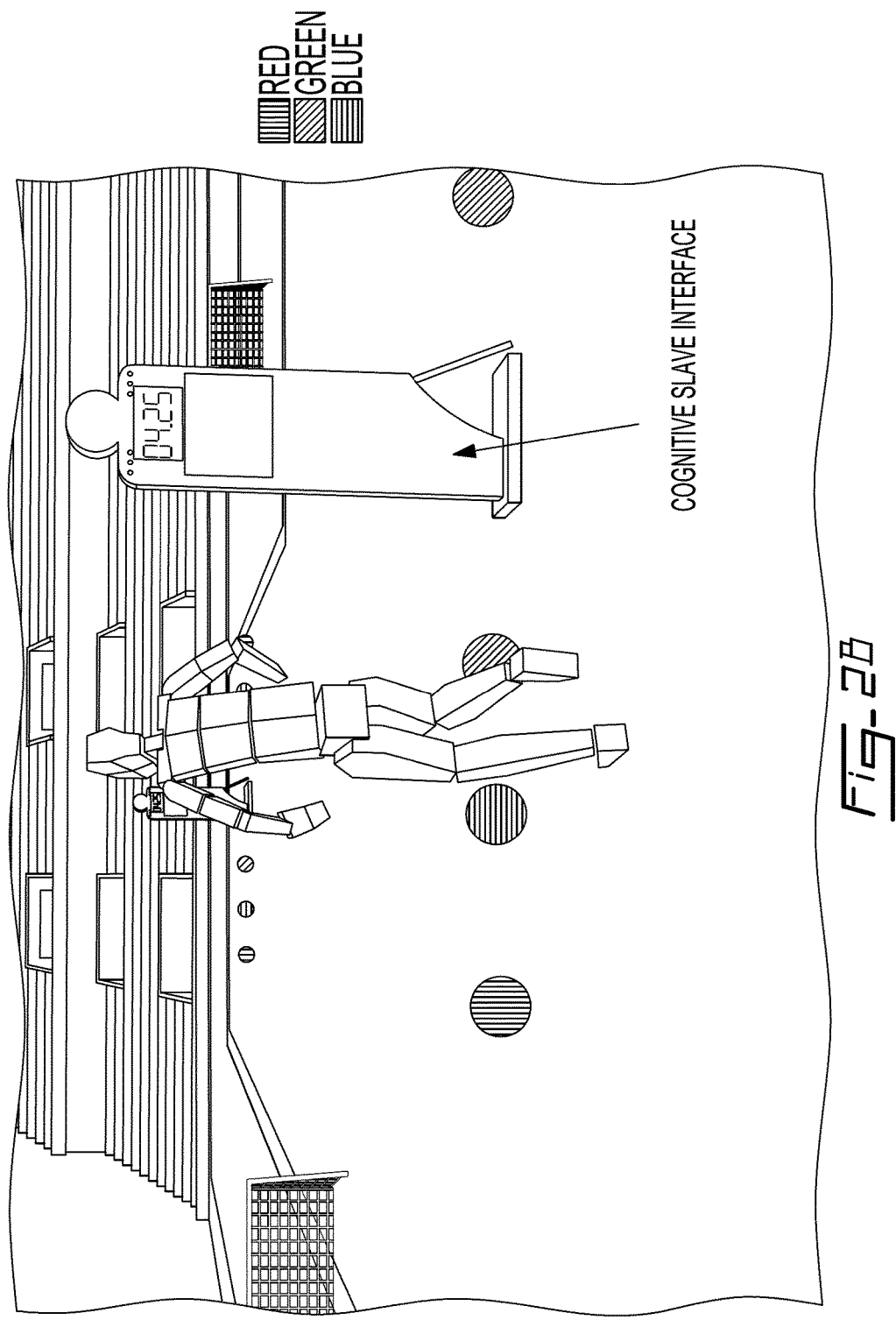

High cognitive processing stimuli used for a western athlete
ACTION 1
arbitrary ideogram to impose a given action to the athlete
(for example: shoot on target)
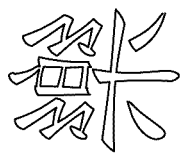
ACTION 2
ideogram to induce a different action to the athlete
(for example: pass the ball)
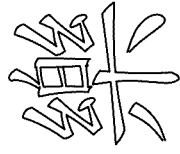
Fig-4

VISUAL STIMULI TO MOVE ON RIGHT
\> ↑ Right Left X 
VISUAL STIMULI TO MOVE ON LEFT
\< ↓ Left Right X 
Fig-5

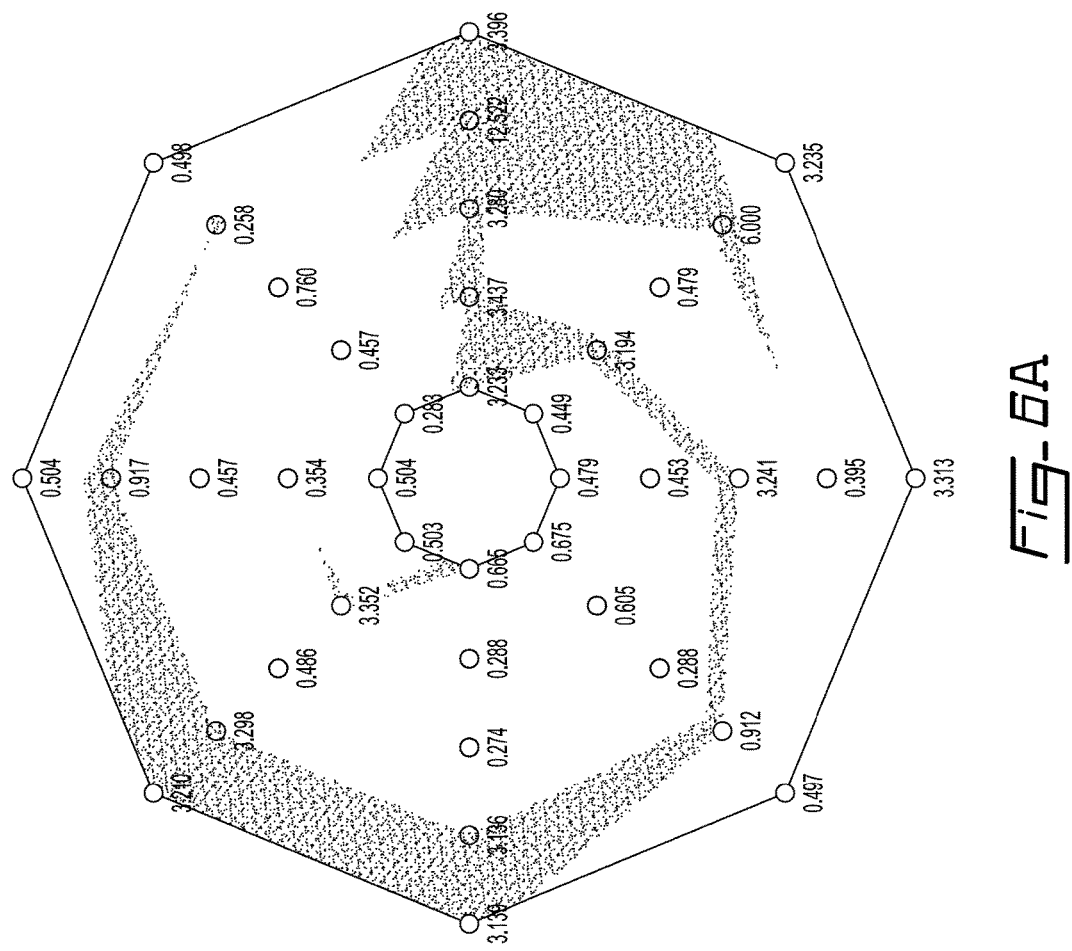

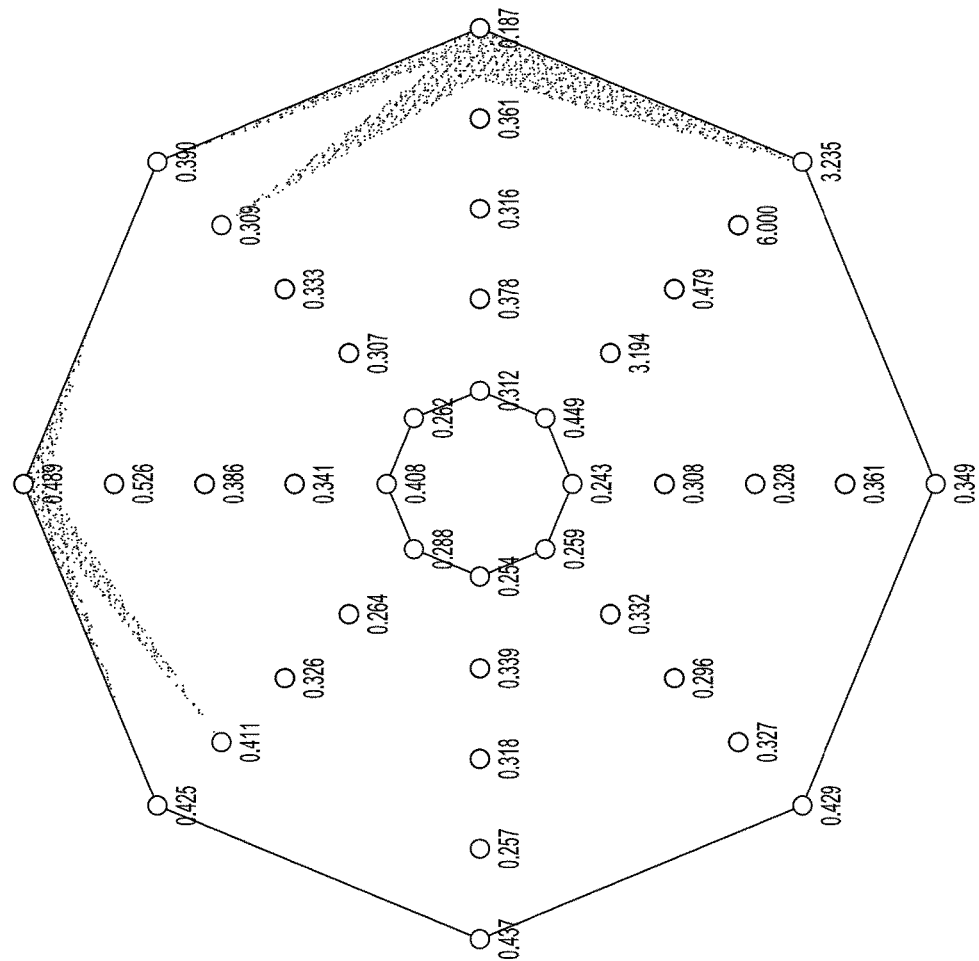

MASTER MODULE
ELEMENTS

MASTER MODULE

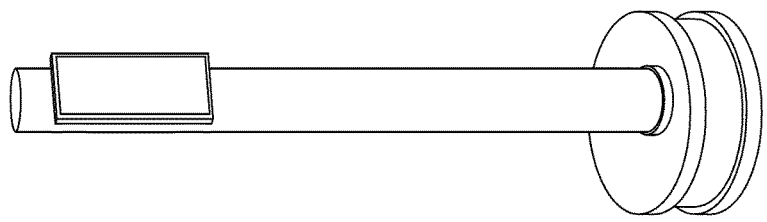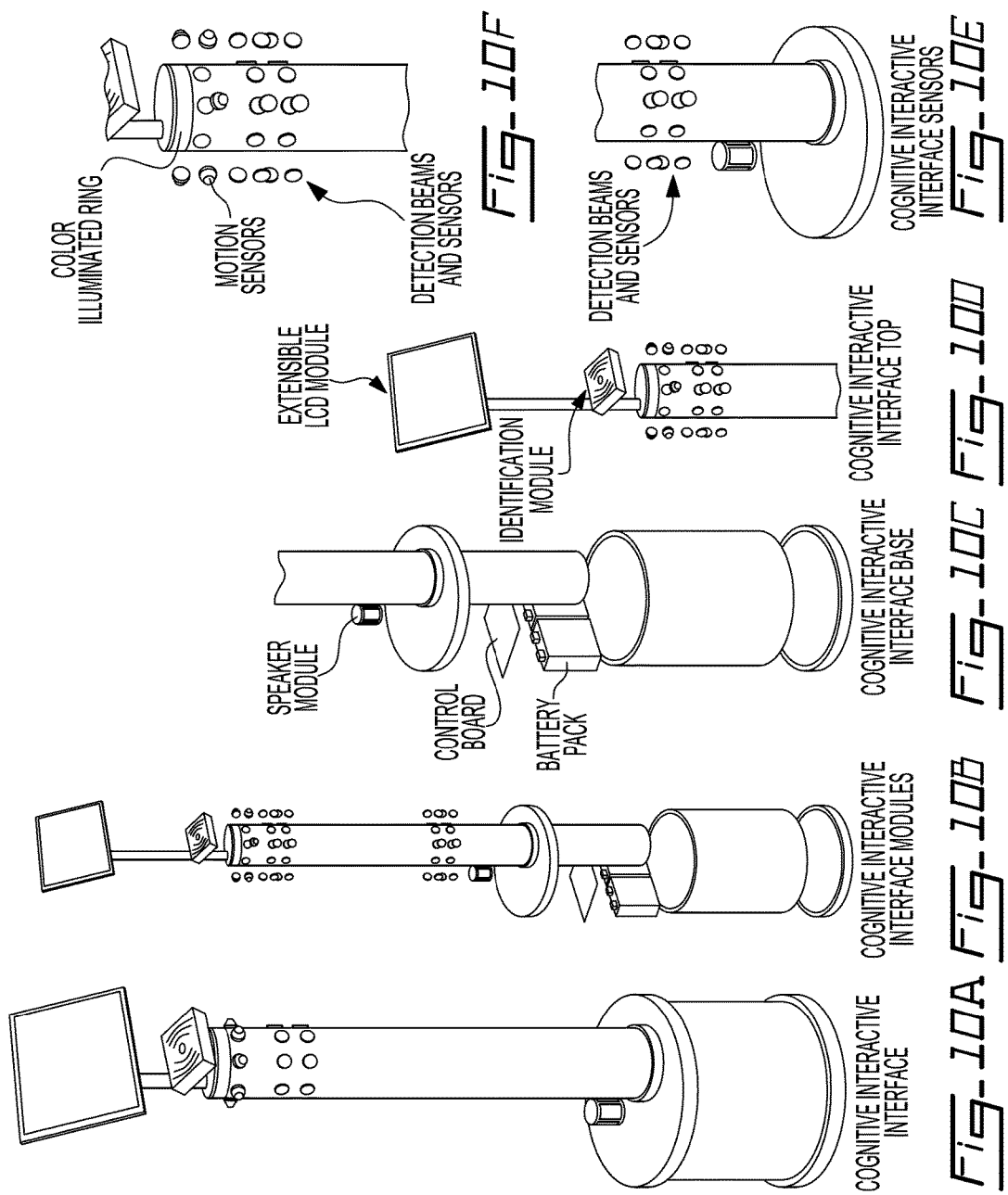

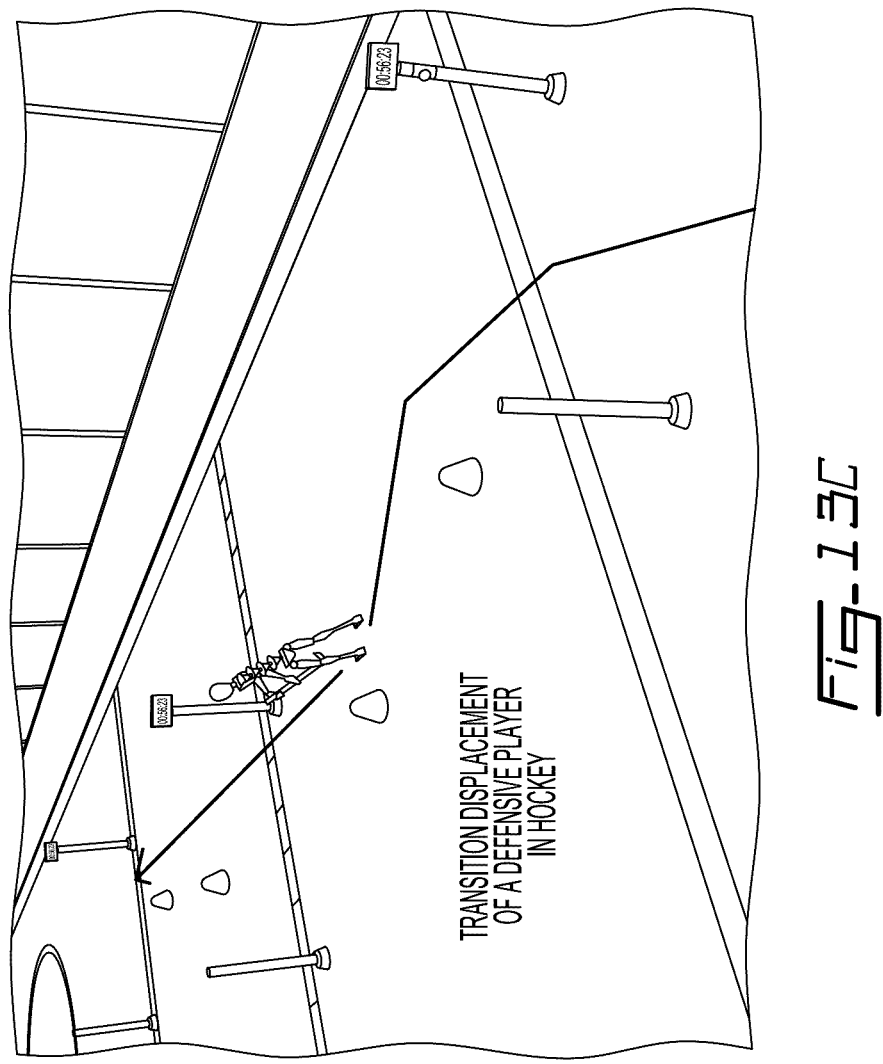

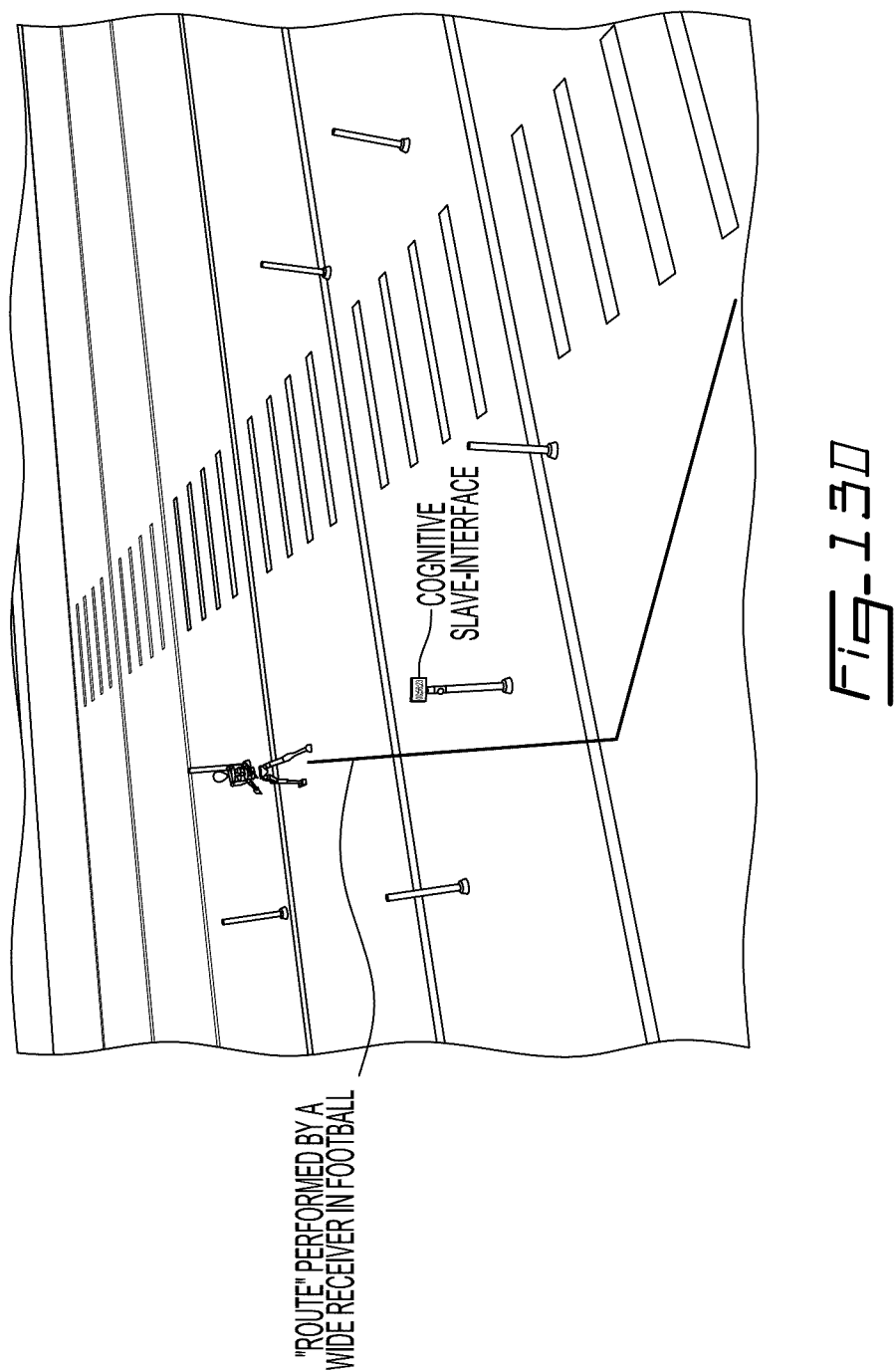

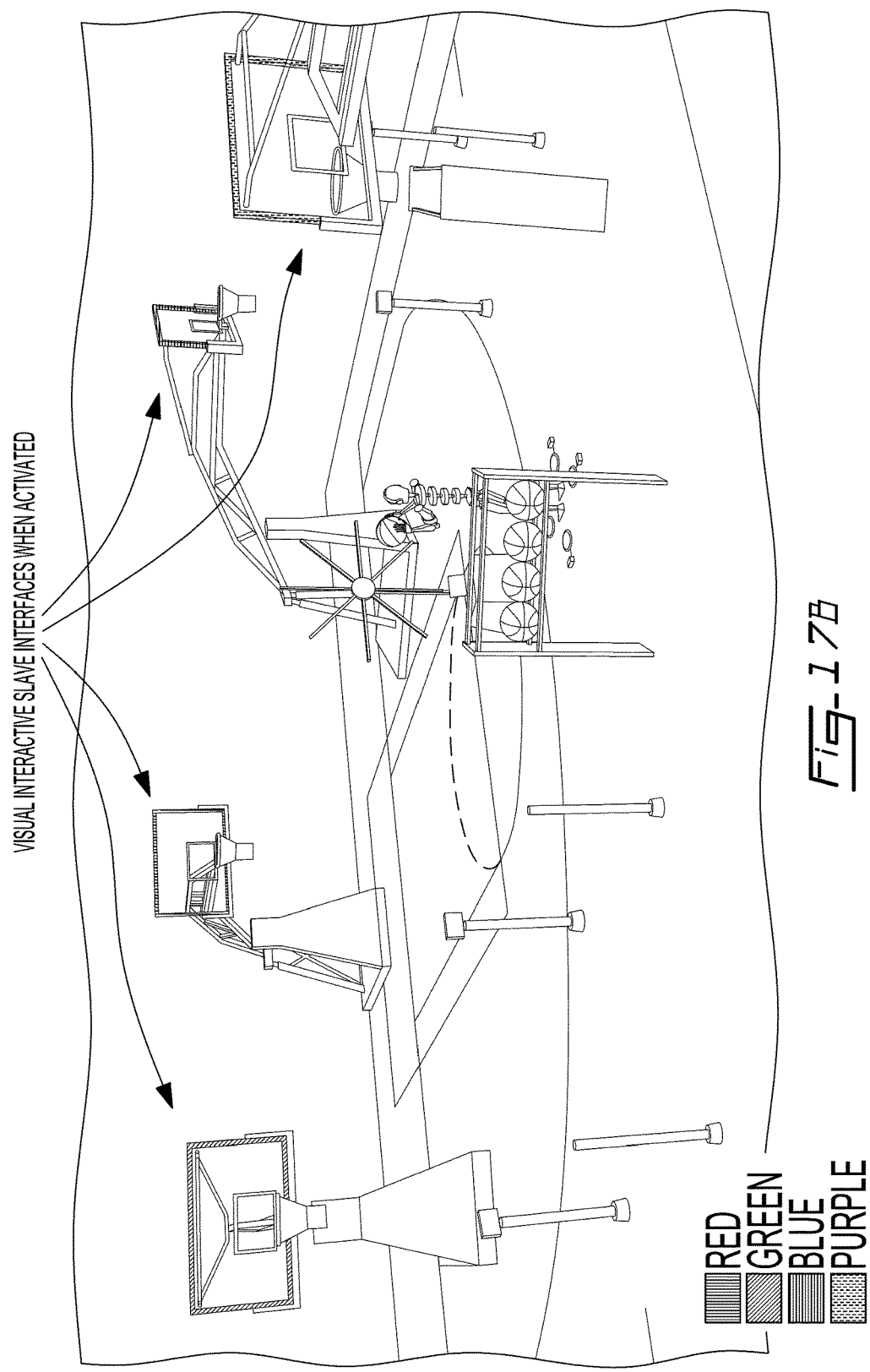

EXAMPLE OF VISUAL-COGNITIVE PRE-STIMULATION ORDERS/PADS IDENTITY

EXAMPLE OF VIBRATORY-VISUAL-COGNITIVE PRE-STIMULATION ORDERS/PADS IDENTITY

| | PAD IDENTITY | | |
|---|---|---|---|
| LEFT BLUE | LEFT RED | RIGHT BLUE | RIGHT RED |
| 1) (single vibration=SV) + blue | SV+red | (double vibration=DV) + blue | DV + red |
| 2) SV+blue | SV+red | DV + blue | DV + red |
| 3) SV+blue | SV+red | DV + blue | DV + red |
| 4) SV + red | SV + blue | DV + red | DV + blue |
| 5) SV+red | SV + blue | DV+red | DV + blue |
| 6) SV+red | SV + blue | DV+red | DV + blue |

ORDERS

FIG-20B

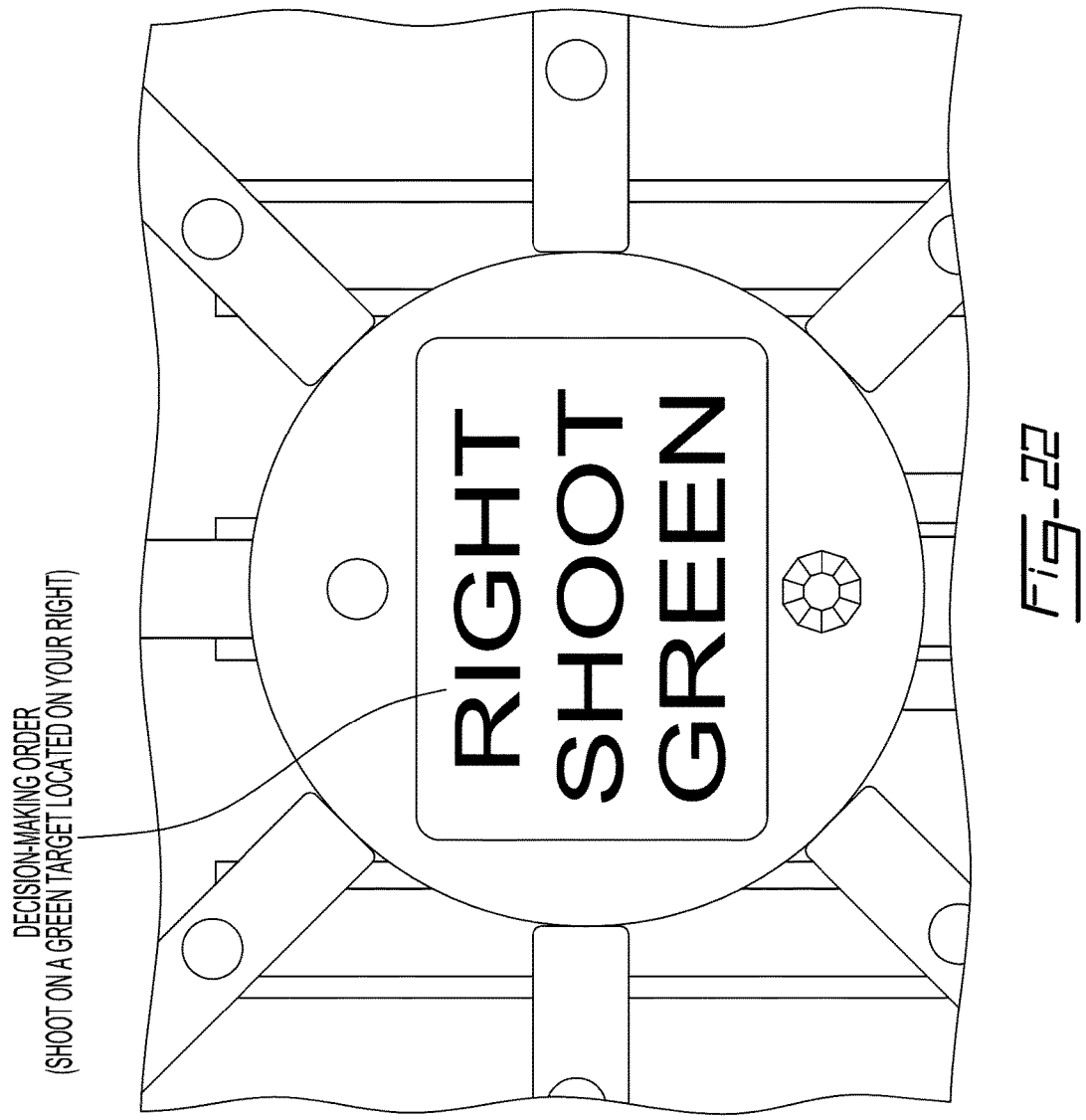

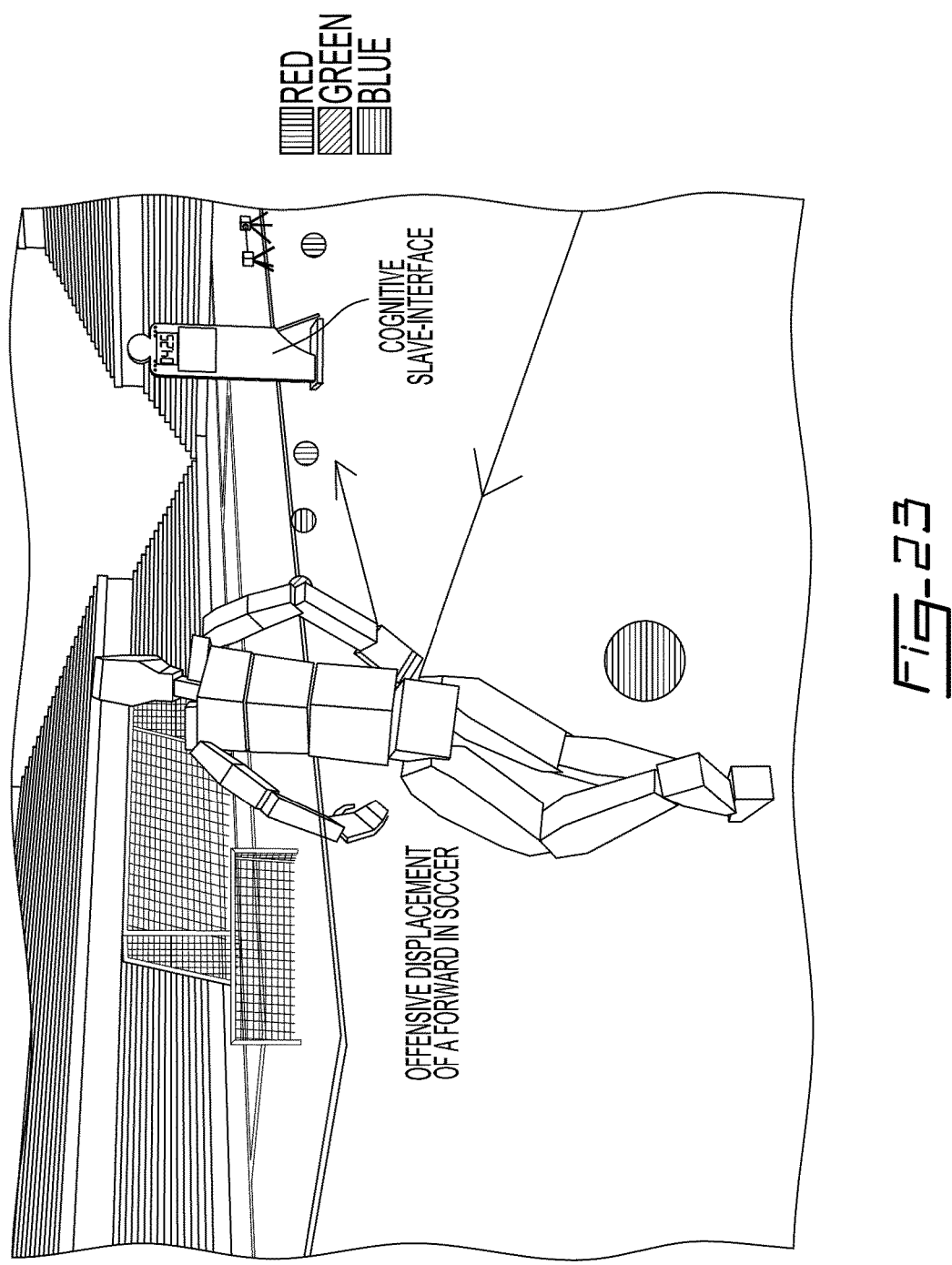

INTERACTIVE COGNITIVE-MULTISENSORY INTERFACE APPARATUS AND METHODS FOR ASSESSING, PROFILING, TRAINING, AND/OR IMPROVING PERFORMANCE OF ATHLETES AND OTHER POPULATIONS

RELATED APPLICATIONS

This patent application is a U.S. National Phase Patent Application claiming priority from PCT International Phase Application PCT/CA2013/050281 of the same title filed Apr. 9, 2013, which claims priority from U.S. Provisional Patent Application 61/691,879 filed Aug. 22, 2012, and which claims priority from U.S. Non-Provisional patent application Ser. No. 13/443,380 filed Apr. 10, 2012 the entireties of which are incorporated herein by reference.

TECHNICAL FIELD

This invention relates to sports training and in particular to multisensorial interactive training systems and multisensorial interactive training methods. The invention also relates to assessment of cognitive function.

BACKGROUND

In sports training there is a growing need for improving athlete performance. A variety of tools, systems and gut feeling type schemes have been tried with varied results. These attempts are regarded insufficient because these attempts lack measurable assessments, measurable base levels, measurable progress and lack a clear indication of correlation between effort expended in employing such tools and systems.

For example, a chronometric gate developed by the Australian company Fusion Sports employs only low level cognitive order cues by stimulating an athlete with color Light Emitting Diode (LED) signals. Another luminous signal stimulating device developed by Dynavision (I-Span) provides the same type of low level cognitive order as the Fusion Sports system employing both light and sound. Wayne Engineering has developed a visual reaction time system with low level visual stimulation. Despite some athletic performance results being achieved, repeatability of training regimes results in variable outcomes from athlete to athlete, which perpetuates reliance on elusive talent which lacks sufficient definition.

Recent research points to the human brain playing a major role in athletic performance.

There is a need to reduce reliance on subjective talent assessments in assessing, improving and attaining athletic performance.

SUMMARY

Existing perceptual-cognitive stimulation systems for sports do not take into account the complexity and the subtlety of cognitive processes in the human brain, and existing devices on the market do not allow corresponding multisensory stimulation (visual-auditory-tactile, separately or combined). It has been discovered that assessing, profiling and training an athlete's response both low and high processing level cognitive multisensory (visual, auditory and vibratory) stimulation improves athlete performance.

It has been discovered that the complexity of cognitive processing is relative to a variety of factors including: cultural references, environmental references, level of education, sport references, level of expertise, etc. Such factors have been found to have an impact on the different cognitive processes taking part in the human brain and can relate to how and athlete can effectively perceive, respond and react to stimulation to improve performance.

It has been discovered that taking into account the physiology of the human visual field, cognitive/multisensory reaction-time correlates well with athletic performance. In view of the finding that reaction-time evaluation limited to the central visual field is insufficient, the proposed solution makes use of cognitive/multisensory reaction-time mapping of multiple sensory and cognitive stimuli over the entire subjects visual field for assessment, profiling and feedback purposes.

In accordance with an aspect of the proposed solution there is provided a method of athletic performance training comprising: establishing with an athlete a sensory semantic language for relating a number of sensory signals to corresponding possible actions, said sensory semantic language being essentially new to the athlete; instructing the athlete to perform an athletic exercise involving skills and full body movement; providing during said exercise a selected one of said sensory signals to the athlete to require rapid discernment by the athlete of the semantic meaning of the sensory signal to correctly chose one of said corresponding possible actions; and determining whether the athlete correctly responds to the selected sensory signal during said exercise.

In accordance with another aspect of the proposed solution there is provided a method of athletic performance training comprising: establishing with an athlete a sensory semantic language for relating a number of sensory signals to corresponding possible actions, said sensory semantic language being essentially new to the athlete; instructing the athlete to perform an athletic exercise involving skills and full body movement; providing during said exercise a selected one of said sensory signals to the athlete to require rapid discernment by the athlete of the semantic meaning of the sensory signal to correctly chose one of said corresponding possible actions; and determining whether the athlete correctly responds to the selected sensory signal during said exercise, processing said reaction time data comprises extracting an athlete performance profile.

In accordance with a further aspect of the proposed solution there is provided an interactive system for athletic performance training, the system comprising: at least one networked cognitive human-machine interface providing to an athlete a selected one of said sensory signals, each cognitive human-machine interface including a processing unit executing machine logic instructions providing said selected one of said sensory signals during exercise; and a networked controller configured to time said provision of said selected one of said sensory signals process a response to said selected sensory signal, said networked controller including a central processing unit executing machine logic instructions determining whether the athlete correctly responds to said selected sensory signal, wherein athletic performance training includes: establishing with an athlete a sensory semantic language for relating a number of sensory signals to corresponding possible actions, said sensory semantic language being essentially new to the athlete; instructing the athlete to perform an athletic exercise involving skills and full body movement;

providing during said exercise a selected one of said sensory signals to the athlete to require rapid discernment by the athlete of the semantic meaning of the sensory signal to correctly chose one of said corresponding possible actions;

and determining whether the athlete correctly responds to the selected sensory signal during said exercise.

In accordance with a further aspect of the proposed solution there is provided a method of athletic performance profiling comprising: establishing with an athlete a sensory semantic language for relating a number of sensory signals to corresponding possible actions, said sensory semantic language being essentially new to the athlete; instructing the athlete to perform an athletic exercise involving skills and full body movement; providing during said exercise a selected one of said sensory signals to the athlete to require rapid discernment by the athlete of the semantic meaning of the sensory signal to correctly chose one of said corresponding possible actions; and determining whether the athlete correctly responds to the selected sensory signal during said exercise, processing said reaction time data comprises extracting an athlete baseline profile.

In accordance with a further aspect of the proposed solution there is provided an interactive apparatus for assessing, profiling, training, and improving performance of subjects, the apparatus comprising: a first cognitive interface configured to provide at least one of a first cognitive, a first visual, a first audio stimulus, said first cognitive interface having a first location; a second cognitive interface spatially separated from said first cognitive interface, said second cognitive interface being configured to provide a at least one of a second cognitive, a second visual, a second audio, second tactile and a second vibratory stimulus; a control system for timing the delivery of said second stimulus with respect to the delivery of said first stimulus to stimulate a subject; and determining a response to at least one of said stimuli, at least one of said stimuli relating to a sensory semantic language pre-established with the subject.

In accordance with a further aspect of the proposed solution there is provided an interactive apparatus for assessing, profiling, training, and improving performance of athletes and other populations, the apparatus comprising: a cognitive interface configured to provide a central visual stimulus in a central field of view of an observer, said observer being required to focus on said central field of view, the cognitive interface being further configured to provide at least one peripheral visual stimulus located in a peripheral vision region of said observer; and a control system for timing the delivery of said peripheral visual stimulus with respect to delivery of said central visual stimulus in order to achieve said assessing, profiling, training, and improving performance of athletes and other populations.

In accordance with a further aspect of the proposed solution there is provided an interactive system for assessing, profiling, training, and improving performance of athletes and other populations, the apparatus comprising: at least one cognitive interface configured to train a response to a plurality of sensorial stimuli.

In accordance with a further aspect of the proposed solution there is provided a method for assessing, profiling, training, and improving performance of athletes and other populations, the method comprising: providing information rich visual stimulation, wherein rich visual stimulation requires an increased level of brain processing resulting in cognitive loading; ascribing meaning to visually similar stimuli; and measuring observer's degree of differentiation between rich visual stimuli.

In accordance with a further aspect of the proposed solution there is provided a method for assessing, profiling, training, and improving performance of athletes and other populations, the method comprising: providing a pre-stimulus for alerting of a subsequent stimulus arrival; providing a stimulus subsequent to said pre-stimulus; and measuring a response to either one of the pre-stimulus and the stimulus.

In accordance with a further aspect of the proposed solution there is provided a method for assessing, profiling, training, and improving performance of athletes and other populations, the method comprising: providing a low order sensory stimulus in the brain's cognitive processing hierarchy; providing a high order sensory stimulus in the brain's cognitive processing hierarchy; and measuring a response to either one of the low order sensory stimulus and the high order sensory stimulus.

In accordance with a further aspect of the proposed solution there is provided a method of athletic performance assessment comprising: establishing with an athlete a sensory semantic language for relating a number of sensory signals to corresponding possible actions, said sensory semantic language being essentially new to the athlete; instructing the athlete to perform an athletic exercise involving skills and full body movement; providing during said exercise a selected one of said sensory signals to the athlete to require rapid discernment by the athlete of the semantic meaning of the sensory signal to correctly chose one of said corresponding possible actions; obtaining decision making data from cognitive sensory human-machine interfaces regarding at least one of said actions; and processing said decision making data according to said semantic meaning of said provided selected one of said sensory signals to extract an athlete baseline profile.

In accordance with a further aspect of the proposed solution there is provided an interactive system for athletic performance assessment, the system comprising: at least one networked cognitive human-machine interface providing to an athlete a selected one of a plurality of sensory signals, each cognitive human-machine interface including a processing unit executing machine logic instructions providing said selected one of said sensory signals during exercise; and a networked controller configured to time said provision of said selected one of said sensory signals and to process a response to said selected sensory signal, said networked controller including a central processing unit executing machine logic instructions determining whether the athlete correctly responds to said selected sensory signal, wherein athletic performance assessment includes: establishing with the athlete a sensory semantic language for relating a number of sensory signals to corresponding possible actions, said sensory semantic language being essentially new to the athlete; instructing the athlete to perform an athletic exercise involving skills and full body movement; providing during said exercise a selected one of said sensory signals to the athlete to require rapid discernment by the athlete of the semantic meaning of the sensory signal to correctly chose one of said corresponding possible actions; obtaining decision making data from cognitive sensory human-machine interfaces regarding at least one of said actions; and processing said decision making data according to said semantic meaning of said provided selected one of said sensory signals to extract an athlete baseline profile.

In accordance with a further aspect of the proposed solution there is provided a method of assessing a concussion comprising: obtaining a first baseline profile at a first point in time prior to a disruptive incident possibly causing a concussion; obtaining a second baseline profile following the disruptive incident possibly causing a concussion; comparing said first baseline profile with said second baseline profile to determine a measure of cognitive impairment due to said concussion.

In accordance with a further aspect of the proposed solution there is provided an interactive system for assessing a concussion comprising: a computerized system for obtaining a first baseline profile; a first baseline profile storage unit configured to store said first baseline profile from a first point in time prior to a disruptive incident possibly causing a concussion; and a comparing unit configured to compare said first baseline profile with a second baseline profile obtained using said computerized system following the disruptive incident to determine a measure of cognitive impairment due to said concussion.

In accordance with a further aspect of the proposed solution there is provided a method of assessing a disruptive incident comprising: obtaining a baseline profile; storing said baseline profile as an initial baseline profile; instructing the athlete to perform said athletic exercise involving skills and body movement after said disruptive incident; providing during said exercise a selected one of said sensory signals to the athlete to require rapid discernment by the athlete of the semantic meaning of the sensory signal to correctly chose one of said corresponding possible actions; obtaining decision making data from said cognitive sensory human-machine interfaces regarding at least one of said actions; processing said decision making data according to said semantic meaning of said provided selected one of said sensory signals to extract an athlete post-incident baseline profile; and obtaining differential performance data between said initial baseline profile and said post-incident baseline profile; and determining whether the athlete experienced a concussion during said disruptive incident from said differential performance data.

In accordance with a further aspect of the proposed solution there is provided an interactive system for assessing a disruptive incident, the system comprising: at least one networked cognitive human-machine interface providing to the athlete a selected one of said sensory signals, each cognitive human-machine interface including a processing unit executing machine logic instructions providing said selected one of said sensory signals during exercise; and a networked controller configured to time said provision of said selected one of said sensory signals and to process a response to said selected sensory signal, said networked controller including a central processing unit executing machine logic instructions determining whether the athlete correctly responds to said selected sensory signal, wherein assessing said disruptive incident includes: obtaining a baseline profile; storing said baseline profile as an initial baseline profile; instructing the athlete to perform said athletic exercise involving skills and body movement after said disruptive incident; providing during said exercise a selected one of said sensory signals to the athlete to require rapid discernment by the athlete of the semantic meaning of the sensory signal to correctly chose one of said corresponding possible actions; obtaining decision making data from said cognitive sensory human-machine interfaces regarding at least one of said actions; processing said decision making data according to said semantic meaning of said provided selected one of said sensory signals to extract an athlete post-incident baseline profile; and obtaining differential performance data between said initial baseline profile and said post-incident baseline profile; and determining whether the athlete experienced a concussion during said disruptive incident from said differential performance data.

In accordance with a further aspect of the proposed solution there is provided a method of post-concussion athletic performance improvement comprising: obtaining said differential performance data; instructing the athlete to perform said athletic exercise involving skills and body movement after said disruptive incident; and providing during said exercise a selected one of said sensory signals to the athlete to require rapid discernment by the athlete of the semantic meaning of the sensory signal to correctly chose one of said corresponding possible actions, said selection of said sensory signals being weighted based on the differential performance data to improve said post-incident baseline profile towards said initial baseline profile if the athlete experienced a concussion.

In accordance with yet another aspect of the proposed solution there is provided an interactive system for improving post-concussion athletic performance, the system comprising: at least one networked cognitive human-machine interface providing to an athlete a selected one of said sensory signals, each cognitive human-machine interface including a processing unit executing machine logic instructions providing said selected one of said sensory signals during exercise; and a networked controller configured to time said provision of said selected one of said sensory signals and to process a response to said selected sensory signal, said networked controller including a central processing unit executing machine logic instructions determining whether the athlete correctly responds to said selected sensory signal, wherein improving post-concussion athletic performance includes: obtaining said differential performance data; instructing the athlete to perform said athletic exercise involving skills and body movement after said disruptive incident; and providing during said exercise a selected one of said sensory signals to the athlete to require rapid discernment by the athlete of the semantic meaning of the sensory signal to correctly chose one of said corresponding possible actions, said selection of said sensory signals being weighted based on the differential performance data to improve said post-incident baseline profile towards said initial baseline profile if the athlete experienced a concussion

BRIEF DESCRIPTION OF THE DRAWINGS

The invention may be better understood by way of the following detailed description of embodiments of the invention with reference to the appended drawings, in which:

FIG. 1 is a schematic diagram illustrating an interactive master human-machine cognitive-multisensory interface in accordance with an embodiment of the proposed solution;

FIGS. 2A and 2B are schematic diagrams illustrating a interactive slave human-machine cognitive-multisensory interfaces in accordance with an embodiment of the proposed solution;

FIG. 4 is schematic diagram illustrating an example of an ideogram employed in cognitive loading-stimulation relative to cultural differences, in accordance with the proposed solution;

FIG. 5 is a schematic diagram illustrating an example of different degrees of cognitive loading imposed by different opposite action stimuli in accordance with an implementation of the proposed solution;

FIGS. 6A and 6B are a schematic diagrams illustrating before and after training cognitive-sensory reaction-time mapping, in accordance with an embodiment of the proposed solution;

FIGS. 10A, 10B, 10C, 10D, 10E and 10F are schematic diagrams illustrating an implementation, and implementation details, of a cognitive slave human-machine interface of a cognitive-multisensory stimulation system in accordance with an embodiment of the proposed solution;

FIG. 11 is a schematic diagram illustrating a remote component of a slave human-machine interface of a cognitive-multisensory stimulation system in accordance with an embodiment of the proposed solution;

FIGS. 13A, 13B, 13C and 13D are schematic diagrams illustrating trigger slave human-machine interfaces in accordance with sport specific implementations of the proposed solution;

FIGS. 17A, 17B and 17C are schematic diagrams illustrating aspects of a cognitive-multisensory stimulation system of the proposed solution deployed in a basketball training context;

FIGS. 20A and 20B are a schematic diagrams illustrating example of sensory-cognitive pre-stimulation orders in accordance with the proposed solution;

FIG. 22 is a schematic diagram illustrating, an order being displayed on the master-interface in accordance with the proposed solution; and FIG. 23 is a schematic diagram illustrating an athlete engaged in a visual-cognitive decision making loop in accordance with the proposed solution.

The presence of the diagrams in this patent application shall not be construed that the diagrams are required for enablement.

DETAILED DESCRIPTION

In accordance with an aspect of the proposed solution an interactive cognitive-multisensory system is provided to assess, profile, train and improve performance of athletes and other populations.

Figure 3A:
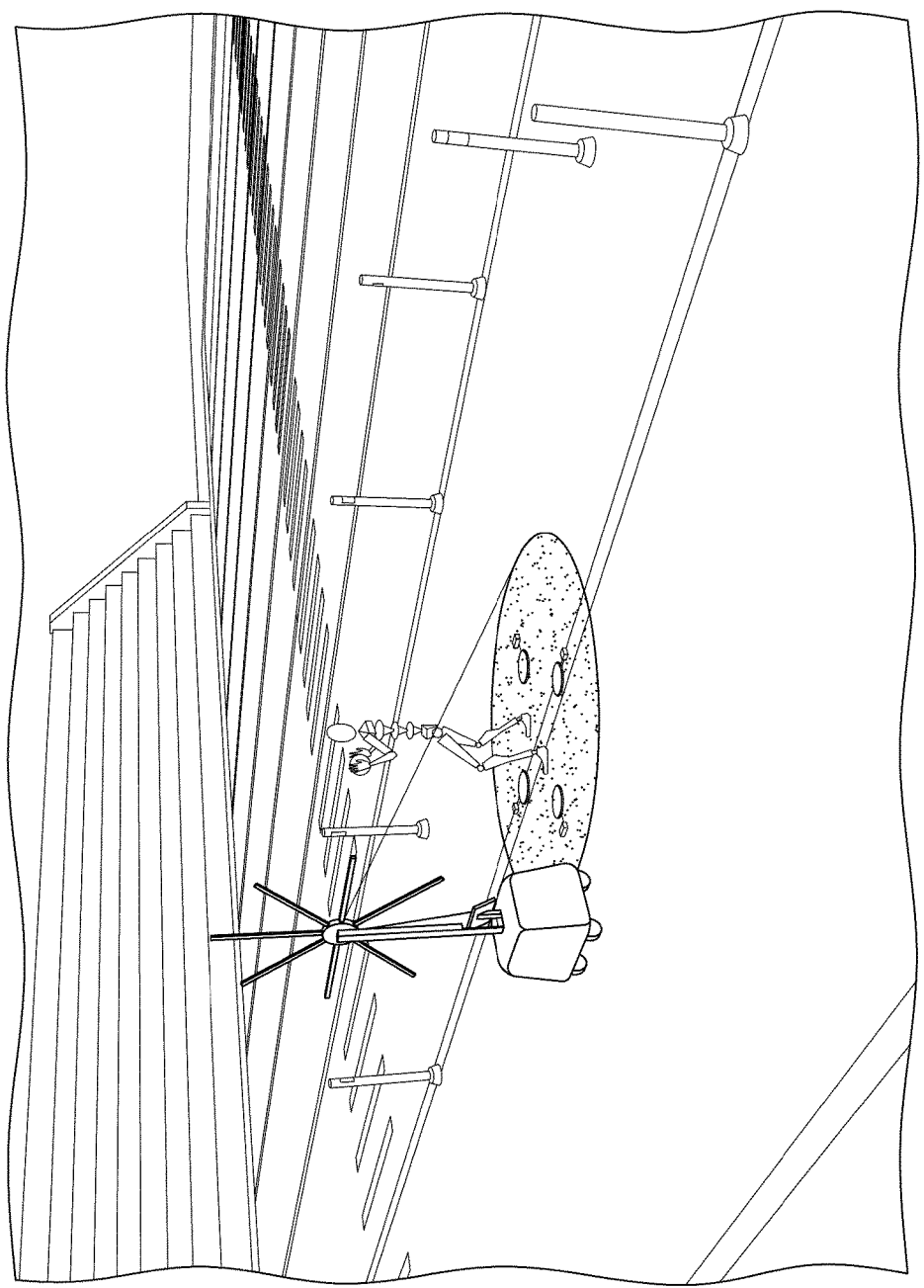
FIG. 3A is a schematic diagram illustrating interaction of an athlete with the master human-machine cognitive-multisensory interface in accordance with an embodiment of the proposed solution.
Figure 3B:
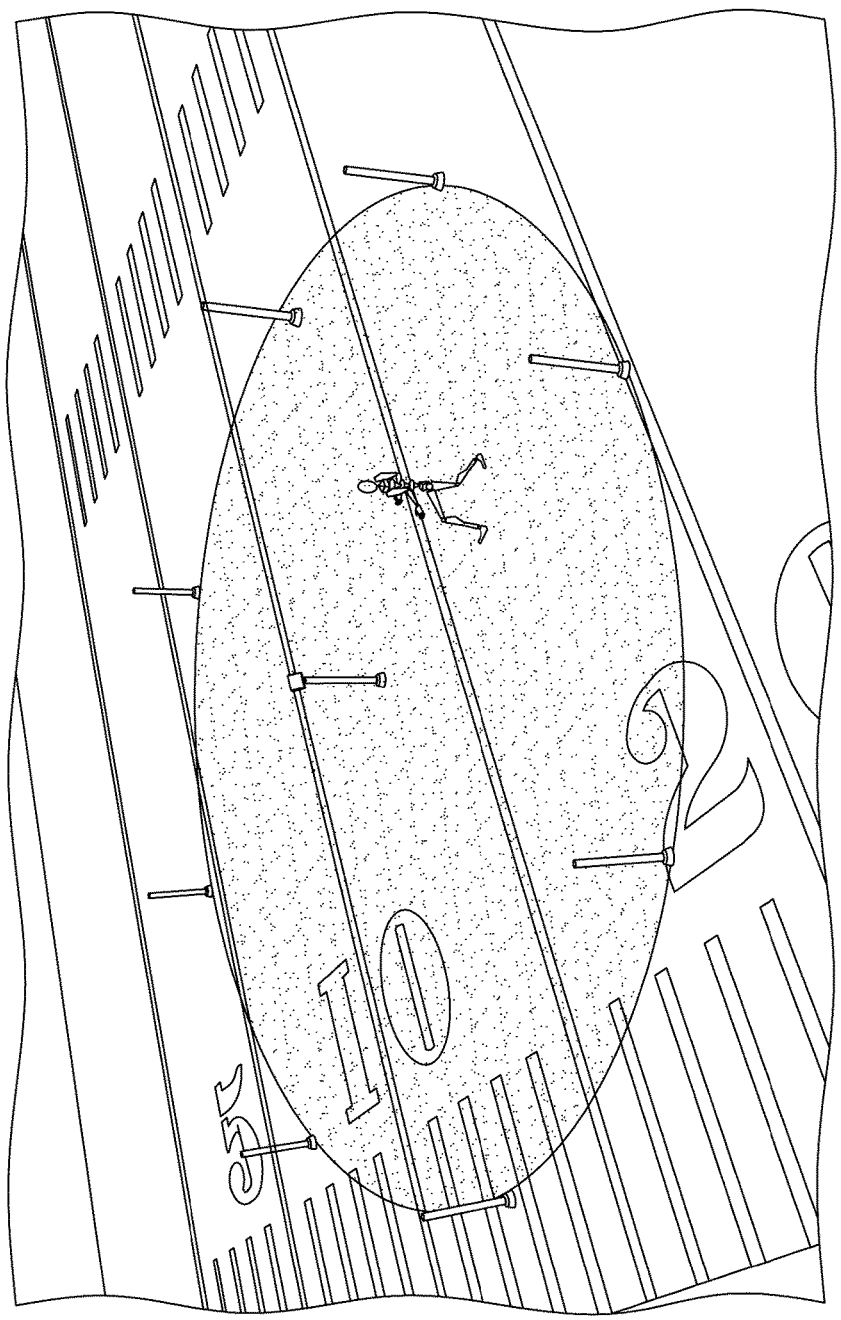
FIG. 3B is a schematic diagram illustrating interaction of an athlete with the slave human-machine cognitive-multisensory interface in accordance with an embodiment of the proposed solution.

In accordance with an embodiment of the proposed solution, the interactive cognitive-multisensory system can be implemented as an apparatus including at least a master cognitive-multisensory human-machine interface, for example as illustrated FIG. 1. The master cognitive-multisensory interface is configured to interact with at least one slave cognitive-multisensory human-machine interface, for example, but not limited to one illustrated in FIG. 2A; and with athletes in (close-to) substantially realistic live sport situations. FIG. 3A illustrates and example of direct interaction between the athlete and the master cognitive-multisensory interface, while FIG. 3B illustrates an example of direct interaction between the athlete and the slave cognitive-multisensory interface. In accordance with a preferred implementation of the proposed solution, the interactive cognitive-multisensory system, a computerized system, directly via the master cognitive-multisensory interface and indirectly via at least one slave cognitive-multisensory interface, simulates sports scenarios typically experienced during real sports action by stimulating different perceptive-cognitive and motor actions typically experienced by athletes during real competition. The slave cognitive interfaces can take different forms preferably having an outer shape which does not interfere with the athlete's performance. For example, a slave cognitive interface is illustrated in FIG. 2B integrated into a standee typically used during practice.

The cognitive/multisensory stimulations provided with the aid of the proposed solution are intended to involve both low and high levels of the brain's cognitive processing hierarchy. The low and high processing levels of an athlete's brain's cognitive processing hierarchy can be assessed, and can thus form part of the athlete's profile, by identifying, on an individual basis, cognitive processing thresholds for types of cognitive simulations. A low cognitive processing level corresponds to a level of brain processing (possibly but not necessarily eliciting a simple and/or a complex motor response) equal or less than a capacity of the athlete to optimally process information in response to a stimulus. Conversely, a high cognitive processing level corresponds to a level of brain processing (possibly but not necessarily eliciting a simple and/or a complex motor response) exceeding the capacity of the athlete to optimally process information in response to a stimulus. It is therefore noted that the cognitive processing threshold is not a number, but rather a distribution of multiple thresholds, each corresponding to specific cognitive stimulus. Notably, when the proposed solution is applied to athlete performance, specific stimuli are relevant to specific sports.

Brain cognitive processing in understood in accordance with the following principles:

i) The simpler the information to be processed, from the point of view of the athlete, the fewer the number of neurons employed in processing thereof. Based on this, the neural network processing such a stimulus is reduced and the information processing time is relatively short, both factors which lead to a relatively rapid response time.

ii) The more complex the information to be processed, from the point of view of the athlete, the larger the number of neurons employed in processing thereof. The neural network processing such a stimulus has a relatively greater expanse and the information processing time is comparatively longer, both factors which lead to a slower response time.

Preferably, the cognitive (multisensory) stimulation generated by the proposed system subject an athlete to complex cognitive situations relative to factors such as: cultural references, environmental references, level of education, sport references, level of expertise, etc. These factors have been found to have a direct impact on the different cognitive processes taking part in the human brain, and examples of stimuli a system implemented in accordance with the proposed solution can include the use of: a word, image, ideogram, different spectrum of sound, different type of vibration, etc. to interact with and stimulate the athlete in an improved way to cognitively simulate uncertain and unpredictable (complex) situations experienced by athletes during sports action. In this sense, in accordance with the proposed solution, a sensory semantic language is employed to increase the complexity of cognitive stimulation. For example, FIG. 4 illustrates the use of ideograms to elicit a response action.

In this context, cognitive-multisensory loading refers to an amount of sensory and cognitive information processed by the human brain (cognitive integration) at a given moment in order to generate a behavioral response (human performance; behavioral-performance). Cognitive-multisensory overloading then refers to an amount of sensory and cognitive information processing which surpasses available neural resources, brain processing time (integration time), attention resources (attentional processing), and physical resources ($O_2$ and glucose consumption in the brain). Cognitive-multisensory overloading is experienced when the amount and complexity of multisensory and cognitive information to which an individual is subjected, exceeds (supraliminal threshold) the capacity (individual threshold) of the individual to process the multisensory and cognitive information. In accordance with the proposed solution, multisensorial-cognitive loading can be employed as a continuum. For example, in accordance with an implementation of the proposed solution, FIG. 5 illustrates visual stimulus commands of different cognitive loading which can be employed during practice by subjecting a western educated athlete to shape recognition tasks using Chinese character strokes (not necessarily a true Chinese character) in order to trigger specific opposite action decision-making. This kind of cognitive subtlety demands a higher level of sensory and cognitive information processing, and potentially an overload, because of the cultural specificity of the stimulus. For certainty, the brain cognitive loading does is not viewed as a limitation with respect to the learning process but as a way to promote more efficient neural pathways of complex cognitive problem solving.

Preferably, implementations of the proposed solution are employed during training with the intent to simulate a real sports context mimicking as close as possible situations experienced by athletes during real competition. For example, auditory stimuli (beeps, calls) can be delivered during training over a background of simulated background noise in order to increase auditory cognitive loading. Auditory stimuli include omnidirectional, mono, stereo, directional and holophonic (three dimensional sound providing both direction and distance cues) across the entire auditory spectrum. Examples of background noise can include simulated stands noise and/or (hockey) organ. As another example, visual stimuli across the entire visual spectrum can be delivered over simulated flashing background noise in order to increase visual cognitive loading. Such flashing noise can simulate flash photography typically encountered during competition. Without limiting the invention, in both of these examples the sensory-cognitive loading increases as the stimulus is harder and harder to distinguish over the interfering background, however other stimuli and other stimuli delivery scenarios can be controllably employed. A visual stimulus example can be a flashing color light against a flashing advertising board. Cognitive loading can also be increased via a complex visual, auditory, tactile, etc. stimulus pattern. For certainty, distracter sensory stimuli, typically random and not necessarily limited to a single sense, can be added to a stimulus pattern in order to increase cognitive loading in an indirect way. For example, an auditory stimulus can be delivered over a background of random flashing lights, etc.

Having described cognitive loading with respect to single stimulus, performance assessment and improvement best correlates when the human visual field characteristics are taken into account. In accordance with a preferred embodiment of the proposed solution, motor-reaction time following stimulus information processing by the brain in response to different stimuli relative to the athlete's visual field is assessed and profiled. Accordingly, processing thresholds mentioned hereinabove are employed as a distribution of a group of thresholds relative to the athlete's visual field. For example, FIG. 6A illustrates cognitive-sensory reaction-time mapping over the athlete's visual field before training, in accordance an embodiment of the proposed solution, and FIG. 6B illustrates cognitive-sensory reaction-time mapping after training in accordance with the proposed solution. In view of the description provided herein above, the mapping relative to the human visual field is normalized to a specific sport, and depending on the sport normalized to a specific player position (center, left, right); team role (goalie, defense, offense, forward, back, striker, etc.) and/or skill level. In accordance with the proposed solution, visual-motor-reaction-time, auditory-motor-reaction-time, tactile-motor-reaction-time, etc. can be selectively, severally or in combination, mapped over the athlete's visual field severally and/or in combination as can be useful in specific training. Without limiting the invention to particular stimuls response information processing, for example performance improvement can be ascertained from the degree of uniformity of the output over the athlete's visual field and output density, being understood that the density is only a visual aid for illustration purposes herein.

The change in cognitive-sensory reaction-time is possible due to brain plasticity and due to a pseudo-automation phenomenon providing a very advanced level expertise in processing complex stimuli following learning and training which makes it possible to attain rapid processing of complex stimuli. Behavioral results post training represent ultra fast decision reaction time to complex stimuli based on a degree of speed and a degree of precision judged against a time required in controlling and correcting the actions of an untrained individual in the same environment or against the length of time required before training. The more complex the cognitive-multisensory training environment relevant to the trained for performance (sport performance/job performance), the more relevant the training is to real life action/performance. To this end, the proposed solution provides examples of complex cognitive-multisensory training:

In accordance with the proposed solution, the apparatus and methods generate stimuli, and preferably provide a learning and training environment, preferably driven by but not limited to a computer system, which exposes an athlete to a cognitive-multisensory overload via sensory and/or perceptual stimulation. Without limiting the invention, the sensory and/or perceptual stimulation includes: unimodal, bimodal and/or multimodal stimulation in performing specific motor tasks.

In accordance with the embodiment of the proposed solution a baseline profile is extracted via a calculation employing multilevel parameters (including, but not limited to: cognitive aspects, visual aspects, motor aspects. etc.) specific and relevant to a given task or field of expertise. For example, measured/detected responses, and measured response times, to a battery of stimuli can be weighted and mapped. The cognitive-multisensory stimulation system then proposes a training protocol taking into account parameters inherent to specific tasks a particular subject is involved in. For example, the training protocol can be based on a calculation which casts mapped values in the baseline profile into mapped values of a training regimen, without limiting the invention casting the mapped values can include applying weighting factors, applying transform functions, ignoring, etc. the mapped values.

In accordance with one implementation of the embodiment of the proposed solution, a sport specific baseline profile can be extracted for the field of expertise of football players in general, however team player position specific profile calculations are employed to suggest team player position specific improvement training such as for: a quarterback and a wide receiver in football. For example ball throwing aspects in the general profile can be nullified in proposing improvement training for a receiver.

In accordance with another implementation of the embodiment of the proposed solution, a team player position specific baseline profile can be extracted directly employing calculation parameters related to a given task. That is, a specific football quarterback baseline profile can be extracted, and quarterback improvement training can be suggested.

Neither implementation is superior. The former can be more thorough while time intensive, however allowing for an assessment regarding team player substitution across team positions. The later can be very specific and time efficient allowing expedient extraction of a baseline profile related to a given task and field of expertise proposing a improvement training specific to the needs of a given subject with respect to his/her current performance and abilities in his/her field of expertise.

Proposing an improvement training with respect to a profile can be understood to include a profile enhancement regimen intended to arrive at a desired (ideal) profile from a baseline profile which can be provided for a given task within a field of expertise (sports, military, task force etc.)

In accordance with the embodiment the proposed solution, an athlete interacts with a cognitive-multisensory stimulation system during assessment, profiling and training:

In accordance with an implementation of the embodiment of the proposed solution the system includes a master human-machine interface, and optionally at least one slave human-machine interface controlled by the master human-machine interface. It would be understood that such human-machine interfaces can be and/or can be driven by a computer system.

Figure 7:
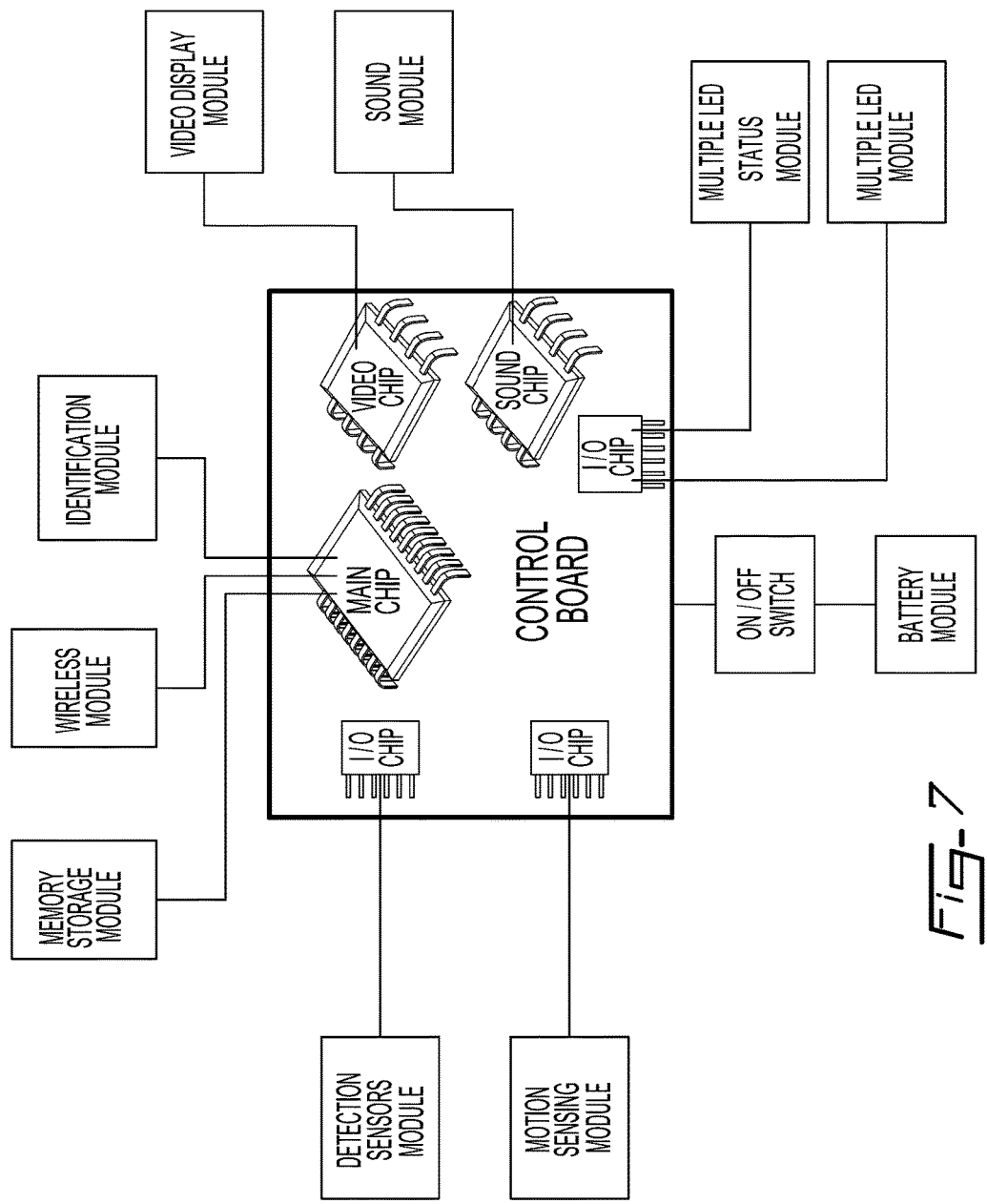
FIG. 7 is a schematic diagram illustrating functional components of a master human-machine interface of a cognitive-multisensory stimulation system in accordance with an embodiment of the proposed solution.
Figure 8B:
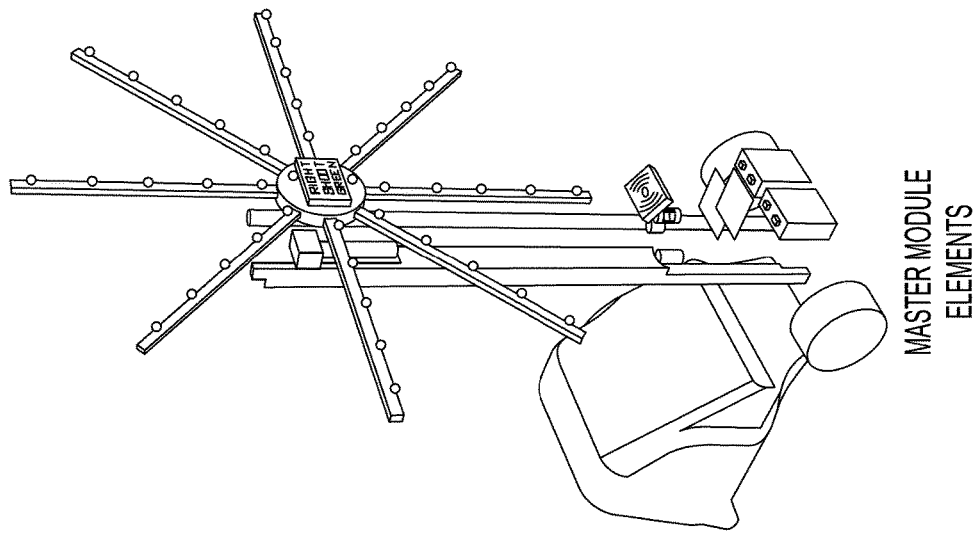
FIGS. 8A, 8B, 8C and 8D are a schematic diagrams illustrating an implementation, and implementation details, of a master human-machine interface of a cognitive-multisensory stimulation system in accordance with an embodiment of the proposed solution.
Figure 8A:
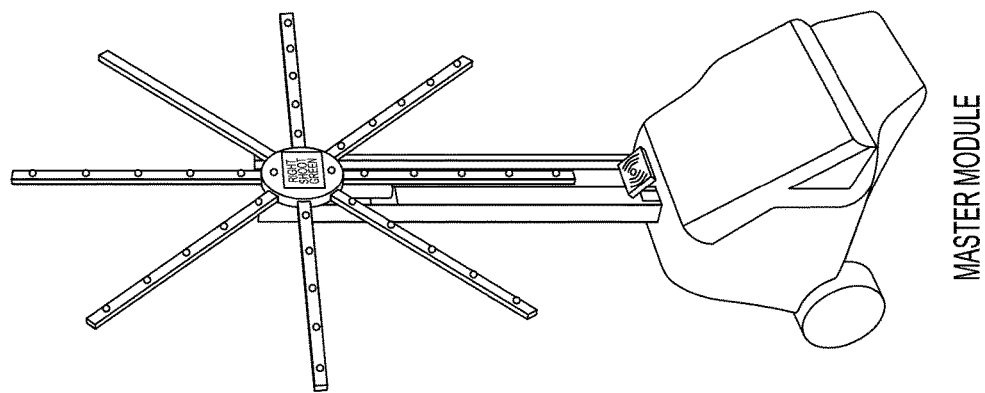

FIG. 7 illustrates functional components of the master interface in accordance with a hardware implementation. The master interface, for example illustrated in FIGS. 8A to 8D, includes a base-section housing. With reference to the exploded view illustrated in FIGS. 8B and 8C, the master interface includes: a main computer board, a control board, a rechargeable battery pack, a speaker module, an identification module, and optionally an actuator motor. The master interface can be provided with wheels to ease portability. Extending from the base section housing is a support-section which includes frame-bars and a linear actuator mounted on the frame-bars for adjusting a stimulation section to allow a vertical adjustment relative to the height of the athlete (or tested subject). With reference to the implementation example illustrated in FIG. 8A to AD, the stimulation section has an overall spoke-and-hub appearance. The stimulation-section includes a group of centrally located components as the hub such as, but not limited to: an LCD screen module, an (RGB) LED, a presence detector, and a camera. Preferably (but not required) configurable arms having a distribution of (RGB) LEDs can be fitted to the hub of the stimulation-section. The arms are configured to provide peripheral visual stimulation via the LEDs encompassing the human visual field as an athlete is positioned in front of the master interface at a corresponding distance in front of the master interface.

Figure 8C:
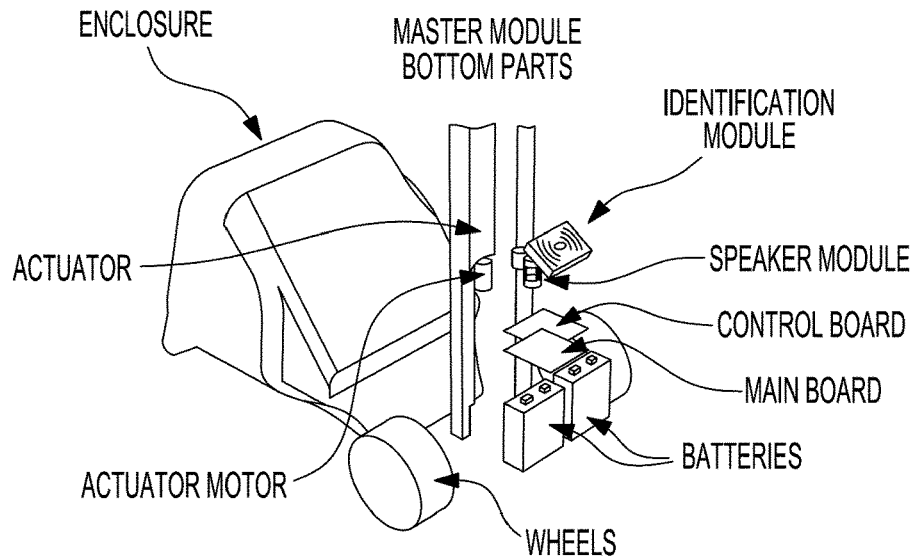
Figure 8D:
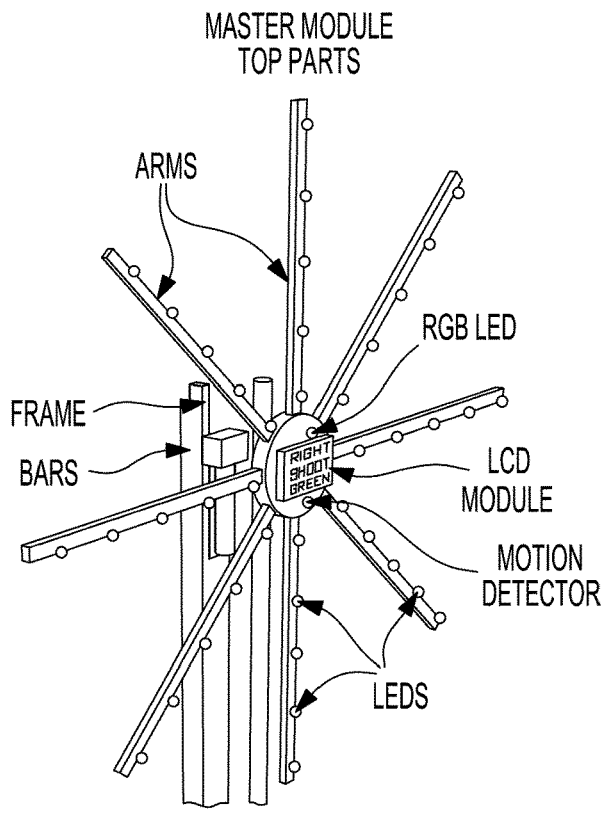

The main computer board of the master-interface includes, without limiting the invention thereto: a Central Processing Unit (CPU) executing machine logic instructions (computer system) of an Operating System (OS) for example MacOS X, linux, android, Windows, etc.; at least one digital input/output controller; main memory; removable memory; a sound controller; a video controller; and a wireless module. Without limiting the invention, a number of components can be implemented in a separate control board as illustrated in FIG. 8C, however it is possible to implement such components on the main computer board. The control board includes a microcontroller configured to receive sensor information from sensors and from the master/slave interface main computer boards, configure the LEDs on the arms of the master-interface, and transmit information to the master/slave main computer boards digital input/output signals. Optionally, one of the control board and the microcontroller includes at least one analog input/output controller.

The microcontroller includes coded logic storage; the CPU and microcontroller executing coded logic instructions implementing functionality, including but not limited to:
  identification (ID) of athletes/subjects;
  ascertain the presence of the athlete/subject in a vicinity of the master interface;
  preferably wirelessly controlling all the interactions between multiple slave-interfaces;
  generating cognitive-multisensory stimulus instructions and preferably wirelessly controlling cognitive-multisensory stimulus output by the master-interface and slave-interfaces;
  assessing cognitive/multisensory motor reaction-time relative to the human visual-field;
  storing interactions generated with respect to a tested subject/athlete;
  storing interactions generated between a tested subject/athlete and the slave-interface(s);
  storing assessment, profiling and training data;
  loading logic instructions and executing logic instructions controlling the main cognitive training and assessment programs; and
  executing logic instructions computing the performance generated by a tested subject/athlete within an evaluation or a training program imposed by the cognitive-multisensory system via the master and slave interfaces.

The master-interface is configured to control: at least one slave-interface, interactions between all slave-interfaces, and interactions between tested subjects/athletes and each interface.

Figure 9:
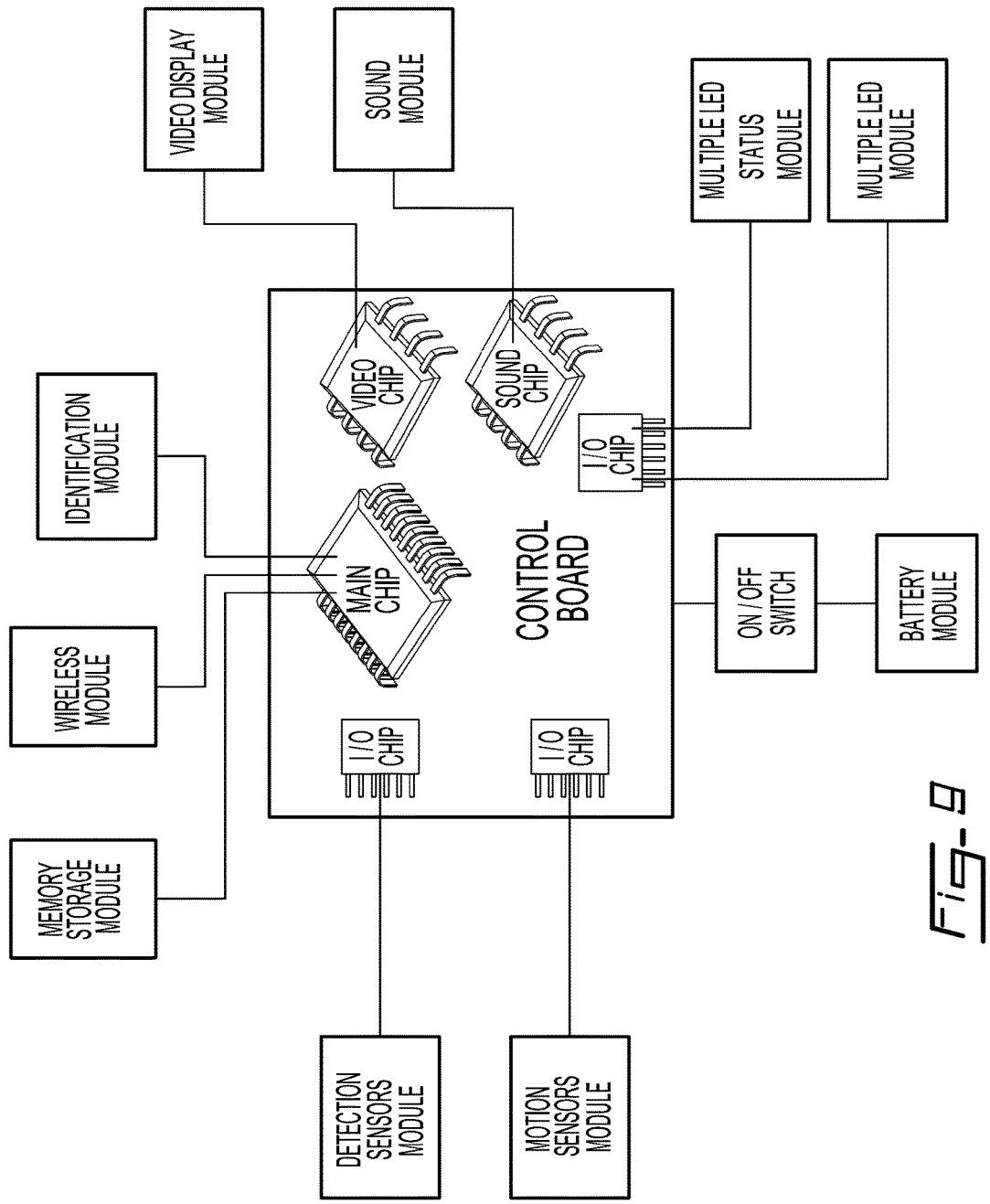
FIG. 9 is a schematic diagram illustrating functional components of a cognitive slave human-machine interface of a cognitive-multisensory stimulation system in accordance with an embodiment of the proposed solution.

With reference to FIG. 9, a cognitive slave human-machine interface, an example of an implementation of which is illustrated in FIGS. 10A through 10F, can include substantially similar functional electronics as the master interface, such as: main computer board, a rechargeable battery pack, an identification module, etc. however preferably with lower processing requirements—the intent being to extend battery powered operation of such slave interface. For certainty, the slave interface need not employ the same OS as the master interface. Without limiting the invention, the controller board can be same as that of the master interface, that is can be or can be driven by a computer system, however configured to interface with specific sensors or stimulators corresponding to the roles of the cognitive slave human-machine interface within the overall cognitive/multisensory stimulation system in accordance with the evaluation or training program driven and coordinated via the master-interface.

In accordance with an implementation of the embodiment of the proposed solution, the cognitive slave human-machine interface illustrated in FIGS. 10A through 10F includes: a (high power RGB) LED stimulator creating a light pattern visible around the slave interface; upper, mid and lower detection sensors each having detection region wrapping 360° around the slave cognitive interface; upper and lower light beam transmitting and receptive elements disposed at angular intervals around the slave cognitive interface; an LCD display module; a sound module; etc. FIG. 11 illustrates a remote component of the slave cognitive human-machine interface for use with selective transmitting and receiving elements of the cognitive slave interface illustrated in FIGS. 10A through 10F. For example, the remote component includes one of: a reflective, flat mirror, corner reflector, etc. element; the combination implementing a beam interrupt sensor. For certainty, features of shape and configuration of the slave cognitive interactive interface illustrated in FIGS. 10A to 10F are not essential; combinations of components mentioned hereinabove can also be implemented in a slave cognitive interactive interface as illustrated in FIG. 2B.

The slave cognitive human-machine interface is configured to operate within the overall cognitive-multisensory stimulation system, for example by receiving instructions from the master-interface, depending on the training program, to generate images on the LCD display module, to generate sounds through the sound module and/or a luminous pattern via the LED. Such instructions received from the master-interface are specific to assessment, evaluation and/or training within the overall training program in-progress. Images are displayed on the LCD display module, and/or sound/luminous pattern is output, as commanded by the master interface, for example subsequent to a given detection sensor being tripped at one of the master interface or the slave interface. The slave cognitive-interface can transmit to the master cognitive-interface spatial presence 360° around the slave cognitive-interface and sensed temporal events (chronometric aspect of the task) for performance calculation(s).

Figure 12:
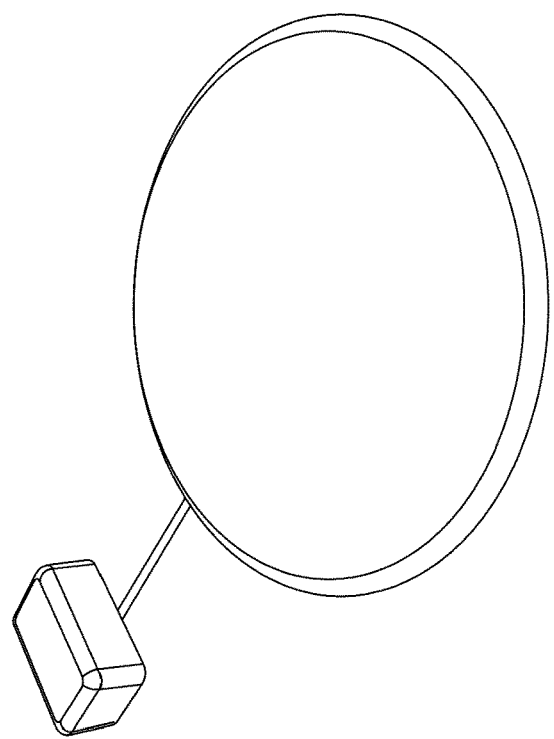
FIG. 12 is a schematic diagram illustrating a tactile slave human-machine interface in accordance with an implementation of the proposed solution.

Additional types of specialized slave-interfaces include cognitive, tactile, ultrasonic, visual, vibratory, etc. having a specific stimulator driven by a scaled down electronics component package. Such slave interfaces can include sensors read by the scaled down electronics component package. Each slave interfaces can exchange information, preferably over wireless communication channels, with other slave interfaces and with the master-interface. For example:

An example of a foot actuated tactile slave human-machine interface is illustrated in FIG. 12. The tactile slave-interface can include the same or scaled down electronics functional components as the master-interface (a main computer board, a control board, a rechargeable battery pack, an identification module) with the I/O chip configured to interface with a pressure sensor module. Without limiting the invention, FIG. 12 illustrates a tactile slave-interface to be stepped on, the proposed solution can be implemented to detect foot kicks, shoulder pushes, hand taps, switch flips, etc. via appropriate configuration.

In accordance with a program driven by the master-interface, the subject is expected to respond to cognitive commands. The tactile slave-interface participates in evaluating cognitive-motor aspects during assessment, profiling and training by recording motor responses of the subject. Multiple tactile slave-interfaces are employed disposed at selected spatial locations depending on the sport/performance and/or role. Responsive to an order sent by the master-interface directly or via a slave-interface, a given tactile slave-interface can be hit/pushed/touched by the subject/athlete. The temporal (when) and spatial (where) aspects of the motor response expected from the subject/athlete are preferably wirelessly transmitted to the master-interface for performance calculation(s). The enables a calculation of a cognitive-motor reaction time.

An example of a presence slave human-machine interface is illustrated in FIG. 3A. The presence slave-interface can include the same or scaled down electronics functional components as the master-interface (a main computer board, a control board, a rechargeable battery pack, an identification module) with the I/O chip configured to interface with an ultrasound transducer module. Without limiting the invention, FIG. 3A illustrates a presence slave-interface having a detection area defined by a projected ultrasonic beam, the proposed solution can be implemented to detect changes in ultrasonic beam back scattering via appropriate beam shape and signal detection level configuration.

Figure 13A:
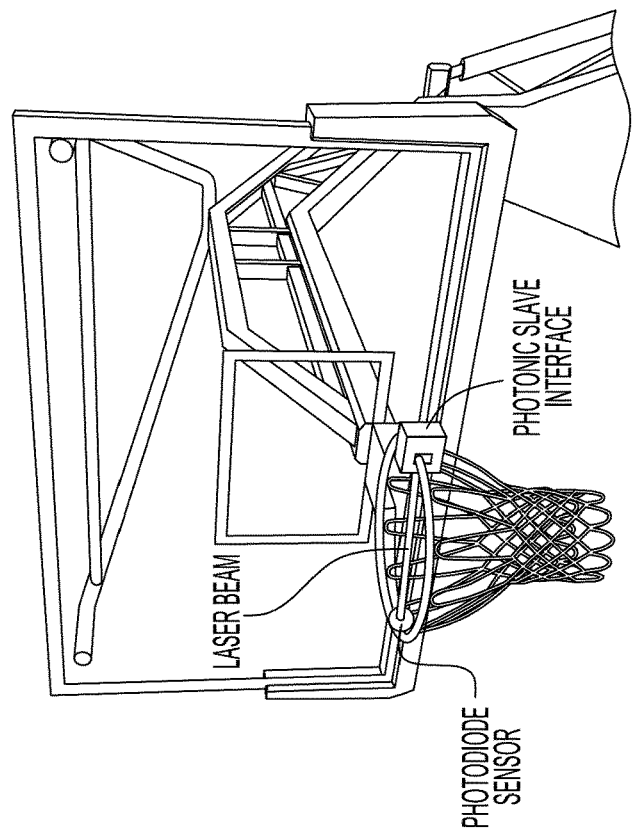
Figure 13B:
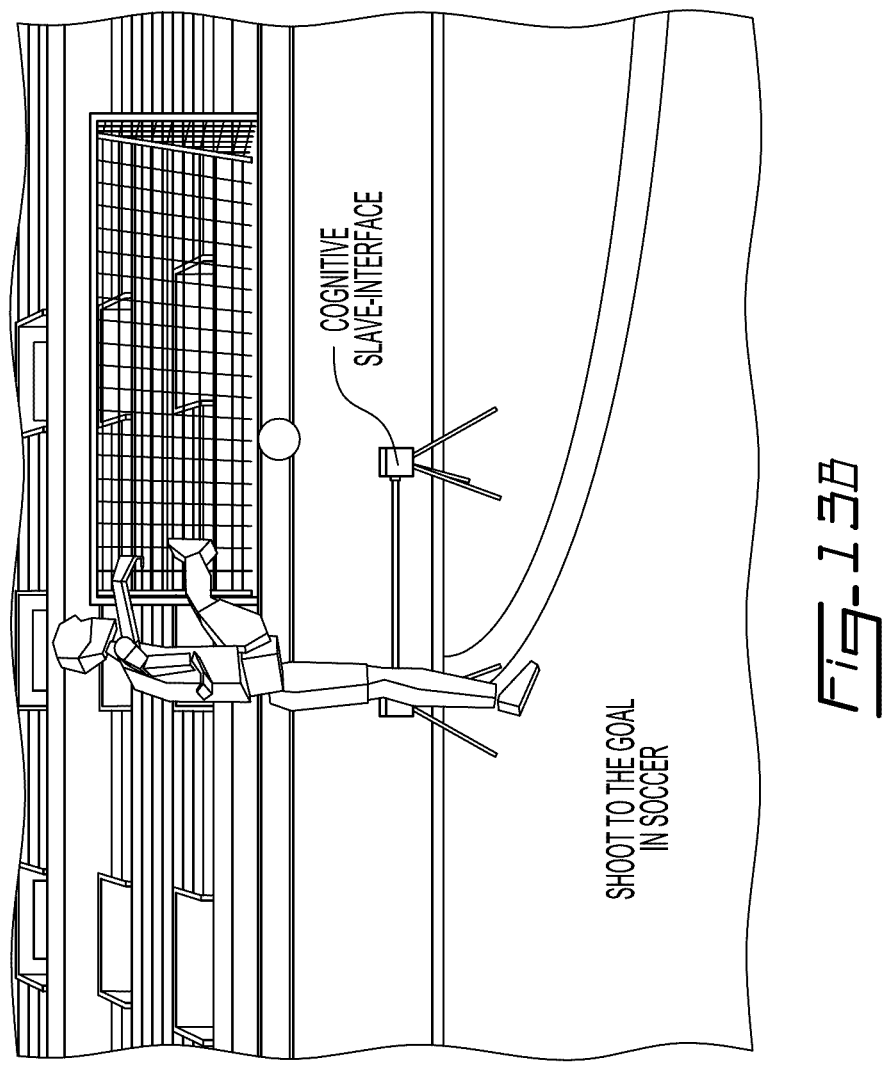

Another example of a trigger slave human-machine interface is illustrated in FIGS. 3B, 13A, 13B, 13C and 13D. The trigger slave-interface can include the same or scaled down electronics functional components as the master-interface (a main computer board, a control board, a rechargeable battery pack, an identification module) with the I/O chip configured to interface with beam interrupt detection module. Without limiting the invention, FIG. 3B illustrates a trigger slave-interface having a detection area defined by number of reflected beams defining a detection pattern for use in American football, FIG. 13A illustrates a trigger slave interface having a laser beam detecting a basket ball falling through the basket, while FIG. 13B illustrates a trigger slave-interface having a light beam detecting a ball kick in soccer, etc. Complex trigger events can be detected by configuring a number of trigger slave-interfaces, for example as illustrated in FIG. 13C for hockey and again for American football in FIG. 13D.

Part of the evaluation programs coordinated by the master-interface, determining sport/performance results can be expected. The cognitive-multisensory stimulation system can measure the ability to throw an object on a target or through a specific zone (puck in a goal or a ball in a basket for example) by using trigger slave-interfaces to detect and transmit to the master-interface, the result of an expected spatial event (puck in a goal). The master-interface employs the information for performance calculation(s).

Figure 14:
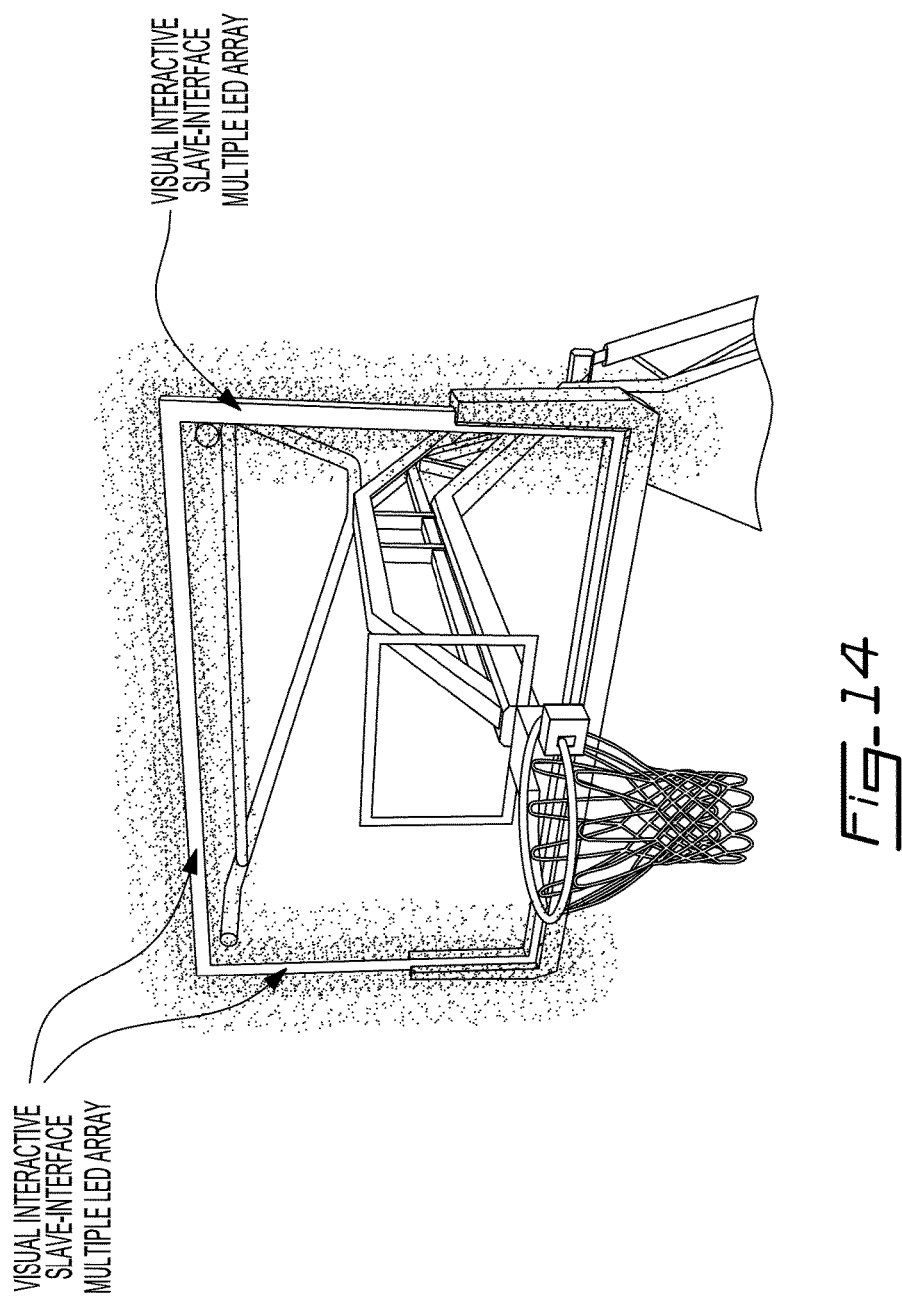
FIG. 14 is a schematic diagram illustrating a visual slave human-machine interface in accordance with a sport specific implementation of the proposed solution.

Besides the input type slave interface examples above, the following represent examples of output type slave interfaces providing sensory cues:

An example of a visual cue slave human-machine interface is illustrated in FIG. 14. The visual slave-interface can include the same or scaled down electronics functional components as the master-interface (a main computer board, a control board, a rechargeable battery pack, an identification module) with the I/O chip configured to drive with a luminous element. Without limiting the invention, FIG. 14 illustrates a visual slave-interface having a luminous border for use in basketball training, the proposed solution can also be implemented as an LED, light panel, projected light beam etc. to implement sport/action specific cues.

As part of the evaluation programs coordinated by the master-interface, a subject's/athlete's reaction to visual orders/cues can be determined. Visual orders/cues are displayed by a visual slave-interface, for example activated in response to a command sent from the master-interface. The expected cognitive-motor response generated by the subject/athlete is recorded by a slave-interface, such as but not limited to: a cognitive slave-interface, a tactile slave-interface, a trigger slave-interface, a presence slave-interface, etc. and sent to the master-interface for performance calculation(s).

Figure 15:
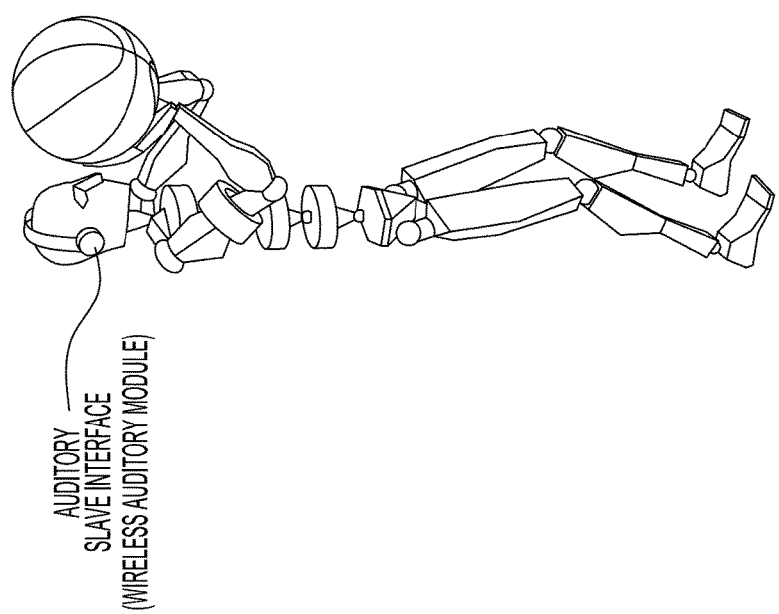
FIG. 15 is a schematic diagram illustrating an auditory slave human-machine interface in accordance with an implementation of the proposed solution.

An example of an auditory cue slave human-machine interface is illustrated in FIG. 15. The auditory slave-interface can include the same or scaled down electronics functional components as the master-interface (a main computer board, a control board, a rechargeable battery pack, an identification module) with the I/O chip configured to drive with a sound producing element. Without limiting the invention, FIG. 15 illustrates an auditory slave-interface having a preferably wireless personalized sound playback device such as a head set or ear buds, the proposed solution can also be implemented as an omnidirectional buzzer, bell, public system announcement source, etc. to implement sport/action specific cues.

Also as part of the evaluation programs coordinated by the master-interface, a subject's/athlete's reaction to auditory orders/cues can be determined. Auditory orders/cues are output by a portable auditory slave-interface, for example activated in response to a command sent from the master-interface. The expected cognitive-motor response generated by the subject/athlete is recorded by a slave-interface, such as but not limited to: a cognitive slave-interface, a tactile slave-interface, a trigger slave-interface, a presence slave-interface, etc. and sent to the master-interface for performance calculation(s).

Figure 16:
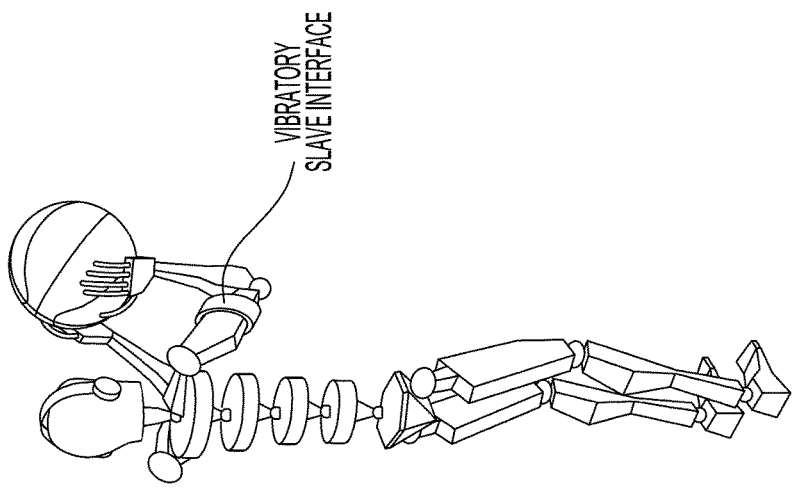
FIG. 16 is a schematic diagram illustrating a vibratory slave human-machine interface in accordance with an implementation of the proposed solution.

An example of a vibratory cue slave human-machine interface is illustrated in FIG. 16. The vibratory slave-interface can include the same or scaled down electronics functional components as the master-interface (a main computer board, a control board, a rechargeable battery pack, an identification module) with the I/O chip configured to drive with a vibration producing element. Without limiting the invention, FIG. 16 illustrates a vibratory slave-interface having a preferably wireless vibration transducer in an arm band device, the proposed solution can also be implemented as a belt, glove, sock, chest protective plate, back protective plate, shoe in-sole, bat/racket/paddle/stick handle, etc. to implement sport/action specific cues. In order for real sports action/job performance to be as close to real as possible during assessment, profiling and training, the vibratory slave-interface should be least cumbersome.

Yet further, as part of the evaluation programs coordinated by the master-interface, a subject's/athlete's reaction to vibratory orders/cues can be determined. Vibratory orders/cues are output by a portable vibratory slave-interface, for example activated in response to a command sent from the master-interface. The expected cognitive-motor response generated by the subject/athlete is recorded by a slave-interface, such as but not limited to: a cognitive slave-interface, a tactile slave-interface, a trigger slave-interface, a presence slave-interface, etc. and sent to the master-interface for performance calculation(s).

In use, a sport/job specific play/performance is assessed, profiled and trained by setting up a scenario in accordance with the needs of a coach/assessor. A master interface and at least one slave interface are set up.

Figure 17A:
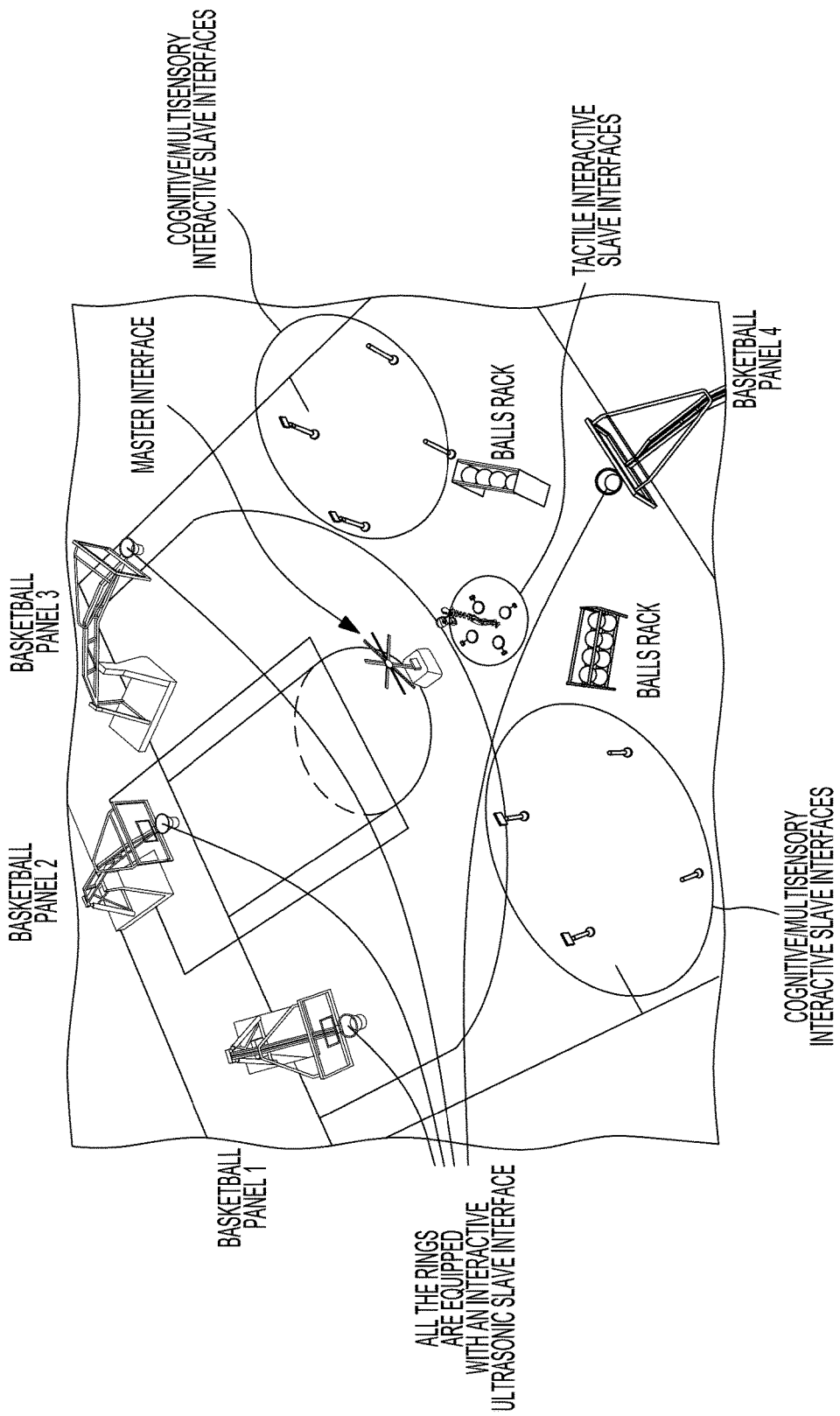

The operation of a cognitive-multisensory stimulation system in accordance with the proposed solution is described in the context of basketball for example. The cognitive-multisensory system is set up on a half basketball court as illustrated in FIG. 17A. The master-interface is positioned in the middle of the court for example near the three-point line. Four tactile slave-interfaces, implemented as tactile foot pads can be disposed in a desired pattern about one meter in front of the master-interface. The tactile slave-interfaces are employed in this set-up to be activated by the subject's/athlete's feet as in basketball foot displacements (and in general full body movement) can be very important in every phase of the game. To the left and right of the tactile foot-pads, cognitive slave-interfaces can be positioned, for example, at 6 meters (18 feet) and 12 meters (37 feet). In the illustrated example, four basketball panels are used and disposed at different positions and orientations with respect to the master-interface and cognitive slave-interfaces. Each basketball panel is equipped with a visual slave-interface and a trigger slave-interface is also set-up on the ring of the basketball basket to detect if the ball has entered the basket. The trigger interface need not be as illustrated in FIG. 13A, it can be as simple as a flap. Ball racks can be disposed on the left and on the right as needed to provide the athlete with balls. Preferably the interfaces communicate wirelessly, however this is not a requirement the interfaces are outside the court area used by the athlete during the program. Notably, the foot pad tactile interfaces are expected not to hinder the athlete and wireless implementations of such tactile slave-interfaces would help reduce such interference.

Prior to the start of a program directed by the master-interface, a check procedure may be launched to ensure that all the parts of the overall cognitive-multisensory stimulation system communicate with each other and ensure readiness for data acquisition, performance calculation(s) and possibility profile extraction. An evaluation, profiling or training program include different types of tasks referred to as loops to calculate a score and to extract a profile relative to the performance of the subject as will be described hereinbelow.

After profile extraction, an optimization program can be recommended by the cognitive-multisensory stimulation system, for example via the master-interface. The optimization program uses specific loops and calculations to train at least some aspects of the subject's profile that have to be improved. For example, such aspects can be identified by comparison between the subject's profile and an expected performance profile specific to a sport/job and role.

Figure 17C:
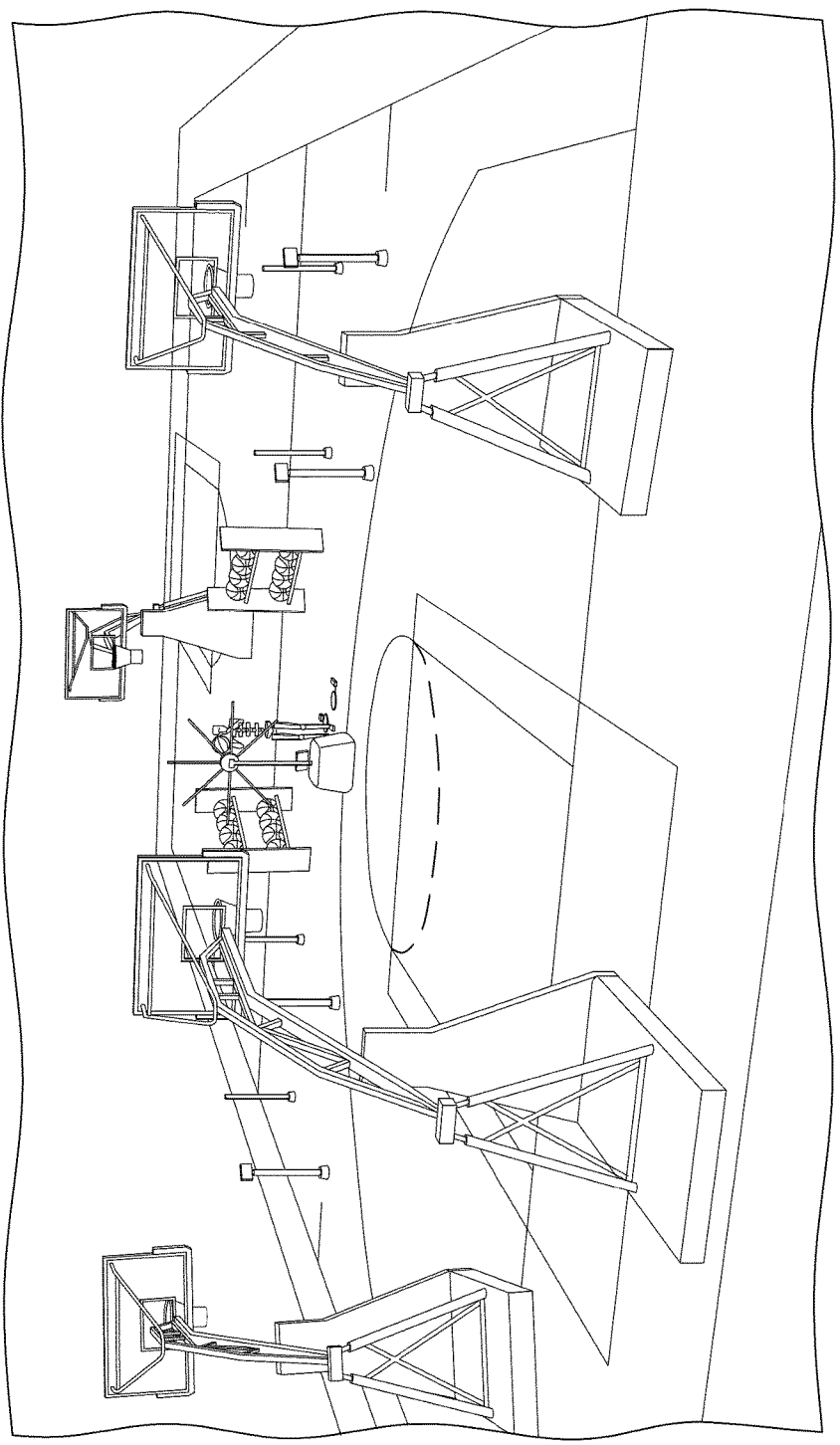
Figure 18:
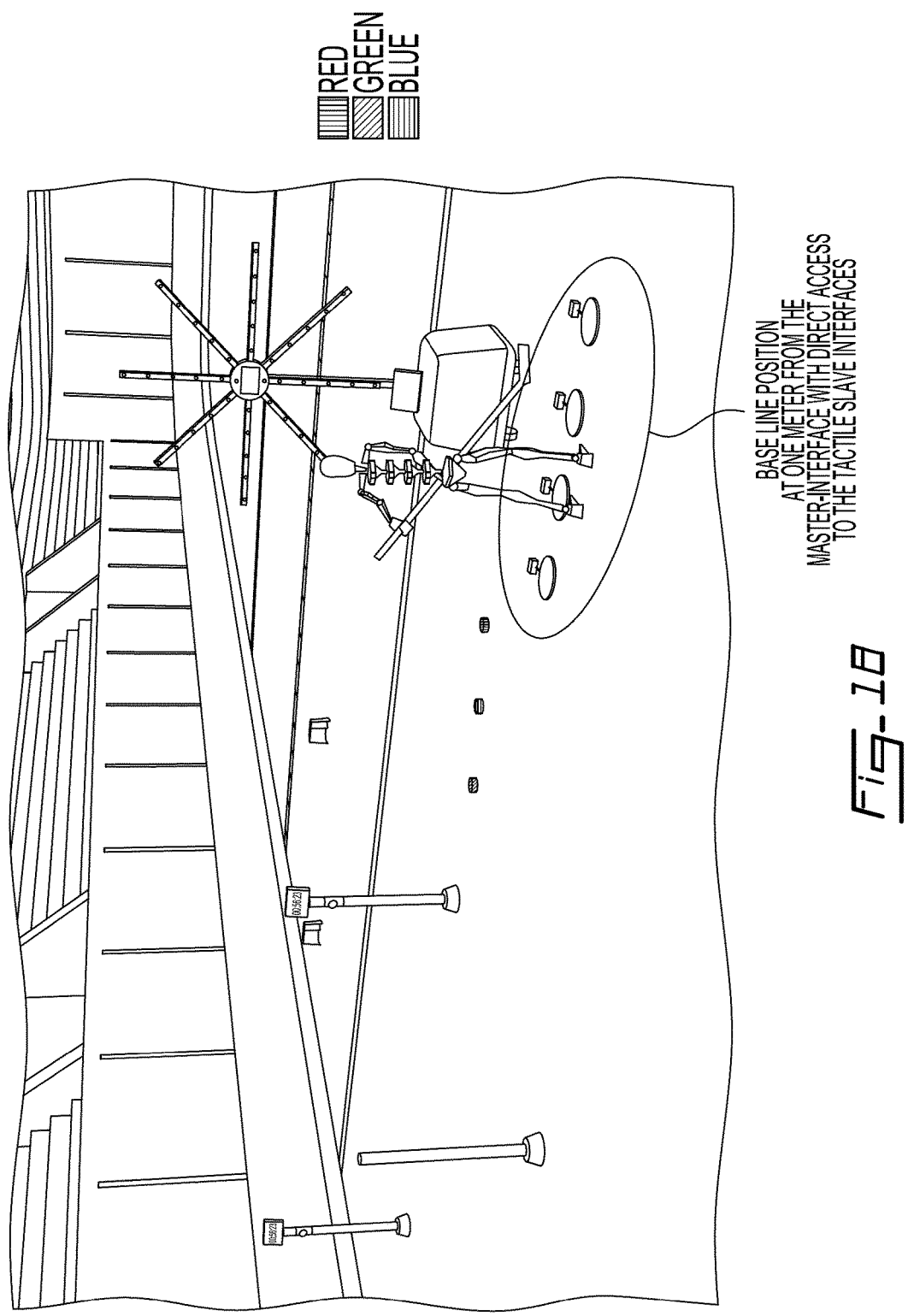
FIG. 18 is a schematic diagram illustrating an athlete at the baseline position in a hockey training context.

Within a chronometric sport context, meaning for sports having tasks to be performed by athletes subject to a best speed-accuracy trade-off, the following example procedure can be followed:

Every time an athlete (subject) has to perform a trial (test), the coach (as the operator of the cognitive-multisensory stimulation system) asks the athlete to stand at a baseline-position. At the baseline position, the athlete has to always look at the central LCD panel of the master cognitive interface. The baseline-position is a location in front of the master-interface in such a way that the spoke arms of the master interface span the athlete's peripheral field of vision, with the hub display of the master interface being located in the athlete's central field of vision. Adjusting the master-interface elevation, for example at the athlete's eye level, can be important to ensure a comfortable viewing for the athlete during the trial. This adjustment of the master cognitive interface is sport dependent, and perhaps also role dependent. FIGS. 17B and 17C illustrate a basketball player standing at the baseline position, while FIG. 18 illustrates a hockey player at the baseline position with knees bent.

Ensuring that the athlete is positioned correctly can be implemented in a variety of ways depending on components employed, cognitive-multisensory stimulation system's processing capacity, degree of sophistication required balanced against hindering the athlete's performance. For example, the LCD screen at the hub of the master interface can have a unidirectional display film, the LCD display being positioned slightly below the athlete's eye level angled up creating a spot from which the LCD can be comfortably observed regardless of what other components are being employed. As another example, the visual cue stimulation LEDs on the arms can be configured to unidirectionally provide the stimulation light output in a pattern intersecting at the location where the athlete's face is expected to be at the baseline position. Both of these examples illustrate defining the athlete's baseline position without physically hindering the athlete's mobility. As another baseline athlete positioning example, footpad tactile slave interfaces, when used, can be positioned in a pattern defining the baseline position. Using footpad tactile slave interfaces can be used to define the baseline position without hindering the athlete for example when the test itself requires dead zones. For example, the basketball player illustrated in FIG. 17A is shown at a baseline position defined by a diamond pattern of footpad tactile slave interfaces wherein the sport requires the athlete to perform long ball throws into baskets and negotiating fallen athletes. The example illustrated in FIG. 18 shows the hockey player at the baseline position in front of a line of footpad tactile slave interfaces defining a line from which the hockey player is to shoot a puck—a diamond pattern of footpad tactile interfaces around the baseline position may interfere with skating and hinder the athlete. Without limiting the invention, a combination of components can also be used, as illustrated in FIG. 3A, wherein footpad tactile slave interfaces in a diamond pattern and a presence slave interface to limit the athlete's body orientation at the baseline position. Last, but not least, the baseline position can be defined by requiring the athlete to actuate a tactile slave interface, as would be the case of a baseball player on a base.

In accordance with a sophisticated example, the athlete's sight can be monitored by a camera of a facial recognition component and/or monitored by a camera of a component configured to determine where the athlete's eyes are pointing. In accordance with another sophisticated example, the athlete's body shape at the baseline position can also be ensured by using a Kinect™ appliance provided by Microsoft. Defining the baseline position is only limited by the available processing power and components employed in the cognitive-multisensory stimulation system.

Returning to the basketball training scenario, the athlete observing the LCD display at the hub of the master interface at arm's length (the athlete standing at a baseline position about one meter from the master-interface) can ensure that the peripheral visual stimulations activated on the master-interface arms will encompass the athlete's visual-field.

In accordance with the proposed solution, with the athlete at the baseline position and before every peripheral visual-stimulation, the athlete will have to integrate a pre-stimulation order defined by pre-stimulations attributes. Depending on the training or evaluation program chosen by the coach, the athlete can be equipped with wireless auditory and/or vibratory slave interfaces and the pre-stimulation attributes can include:

Visual-Cognitive: different levels of visual-cognitive orders can be displayed on the central LCD;

Sensorial: an auditory or a vibratory stimulation;

Multi-sensorial: audio-visual, an audio-vibratory, a visual-vibratory or a visual-auditory-vibratory stimulation combination;

Sensory-Cognitive: a mix (FIGS. 20A and 20B) of visual-cognitive (FIG. 19) and a sensorial stimulation; or Cognitive-multisensory: a mix of a visual-cognitive and a multi-sensorial stimulation.

Figure 21:
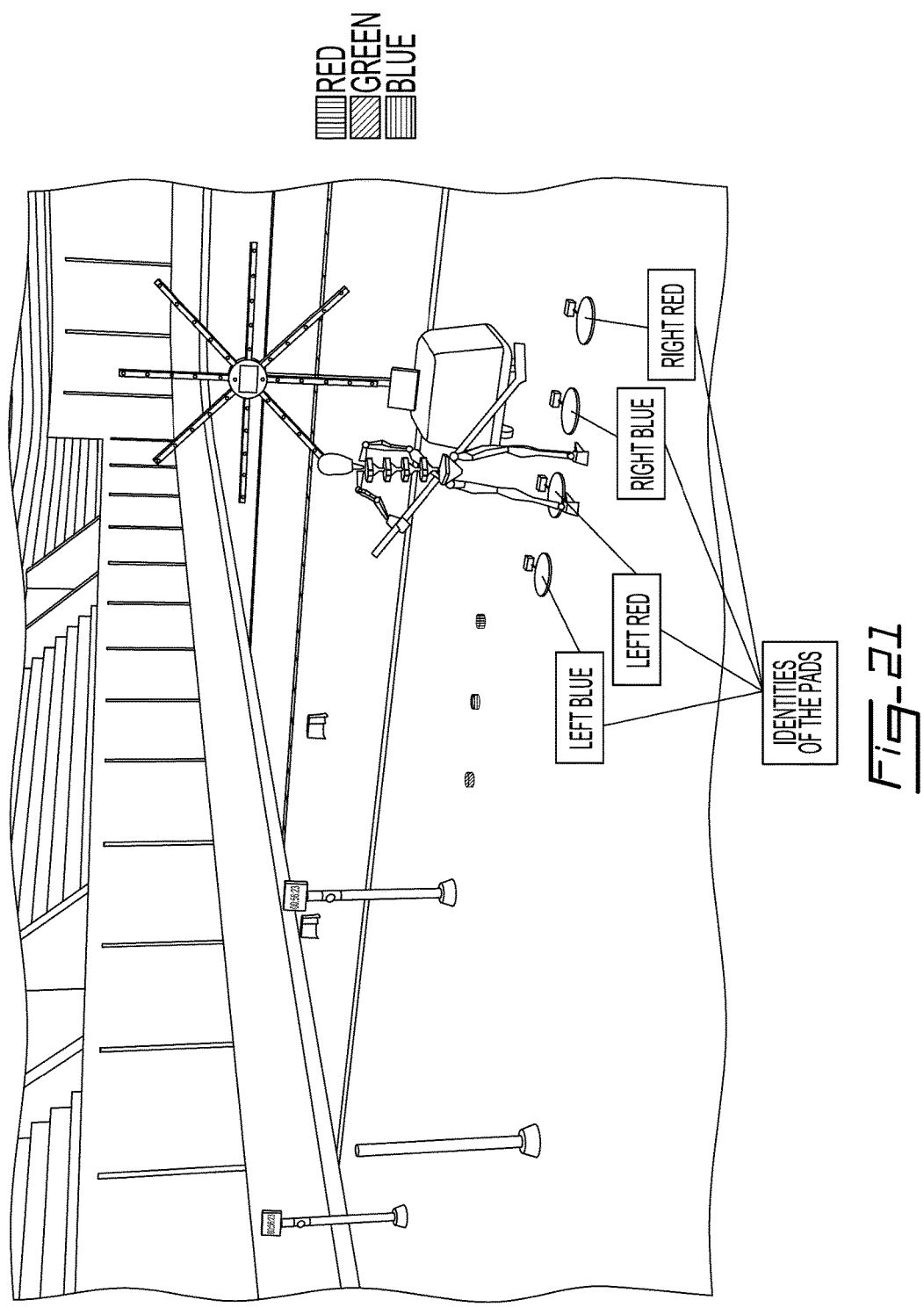
FIG. 21 is a schematic diagram illustrating, by way of example, an association between prestimulation orders and tactile slave interface in accordance with the proposed solution.

In order to emphasize that the invention is not limited to a particular sport, the expected footpad trigger slave interface actuation expected in response to the pre-stimulation orders is illustrated in FIG. 21 for hockey. The number of the tactile slave interfaces (footpads) can be varied by the coach to increase the degree of difficulty (ex: 2, 4 or 6 pads etc. . . . ) in the identification and interaction process with slave interfaces during pre-stimulation.

The pre-stimulations orders, such as but not limited to ones illustrated in FIGS. (4, 5) 19, 20A and 20B, displayed by the master-interface, for example as illustrated in FIG. 22, correspond to the identity of a tactile-interface to be triggered when a peripheral visual-stimulation is displayed on the master-interface arms. The identity of a tactile-interface can be selected by the coach via pre-stimulation attributes, to increase the difficulty of the cognitive identification process. (ex: alpha, omega, beta+single or double tone single or double vibration of the arm).

After the display of a pre-stimulation order, a peripheral visual-stimulation is presented on a master-interface arm by the illumination of an LED. The location of the peripheral visual-stimulation on the master-interface arms and the inter-stimulation delay time between a pre-stimulation order and a peripheral visual stimulation are randomized and controlled by the master-interface program. The randomization ensures that the athlete employs a high level of attention. After perception of a peripheral visual-stimulation, the athlete has to trigger the appropriate tactile-interface (footpad) corresponding to the identification provided by the pre-stimulations order. The process including pre-stimulation order, peripheral visual-stimulation and the motor response (triggering the footpad) is called visual-cognitive/multisensory reaction-time loop. The number of successive visual-cognitive reaction-time loops can be set by the coach within a given evaluation or training program. The visual cognitive/multisensory reaction-time loop is used by the system to build a cognitive/multisensory reaction-time mapping as illustrated in FIG. 6A or 6B for the athlete. This mapping is a part of the performance calculation.

After a set of visual-cognitive/multisensory reaction-time loops, the master-interface displays a pre-decision-making order. The athlete has to integrate and to skillfully react to a pre-decision-making order defined by pre-decision-making attributes, including:

Visual-Cognitive: different level of visual-cognitive orders can be displayed on the hub LCD;

Sensorial: an auditory or a vibratory stimulation output on auditory/vibratory slave-interfaces;

Multi-sensorial: an audio-visual, an audio-vibratory, a visual-vibratory or a visual-auditory-vibratory stimulation;

Sensory-Cognitive: a mix of visual-cognitive and a sensorial pre-stimulations; or Cognitive-multisensory: a mix of a visual-cognitive and a multi-sensorial pre-stimulations.

These pre-decision-making orders displayed via the master-interface correspond to a sport's specific action in terms of full body movement (displacement, shoot, pass, tackle, block, swing, etc.) that the athlete has to perform. With reference to FIGS. 22 and 17B, the order instructs a basketball athlete to "tap right footpad and shoot the ball in the basket on the green panel." With reference to FIGS. 22 and 21, the order instructs a hockey player to "move to the right and shoot the green puck in the goal." Preferably, the specific sport action entails "skillful full body movement" meaning a physical task similar to or commonly done within the context of an athletic (job) performance, and which involves the athlete's skillful physical movement within an area of performance activity.

The athlete has to cognitively integrate the pre-decision-making order as fast as possible to perform a sport specific action, for example an expected full body movement/displacement in an appropriate direction towards an appropriate prepositioned cognitive slave-interface within a minimum time window (irrespective of skill for example a sprint). The complexity of the pre-decision-making orders can be customized by the coach via pre-decision-making attributes, to increase the difficulty of cognitive loading to utilize, practice or improve a skill (ex: alpha, omega, beta+single or double tone single or double vibration of the arm, etc.)

Figure 19:
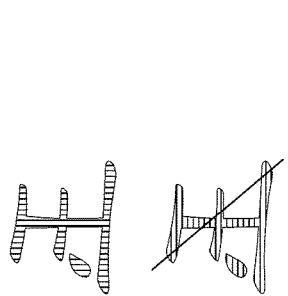
FIG. 19 is a schematic diagram illustrating an example of visual-cognitive pre-stimulation orders in accordance with the proposed solution.
Figure 20A:
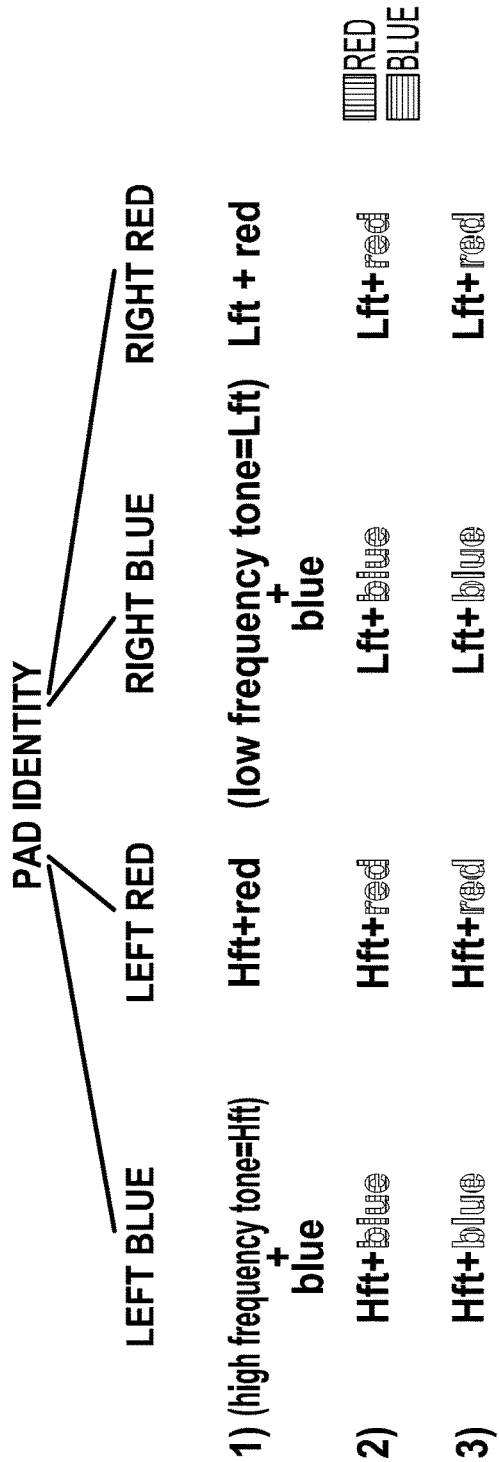

With reference to pre-stimulation orders and pre-decision-making orders, in accordance with the proposed solution, a sensory semantic language is employed via the selection of the attributes. For certainty the sensory semantic language is not limited to displayable orders as illustrated in FIGS. 19, 20A and 20B, and can include other sensory stimulation patterns. Multiple slave interfaces, and appropriately the master interface, are employed in combination either severally or simultaneously to create an interactive environment providing a rich, complex and diverse scenario generation environment relative to human performance, the sensory semantic language provides a mapping to corresponding possible sports (job) actions. It would be understood that using the computer system, a sensory semantic language can be selected, possibly at random, from a large selection of sensory stimuli not necessarily visual or auditory; possibly some information can be retained between sensory semantic language selections to reduce repetition.

The sport's specific action can be adapted for:
a targeted sport;
the team role (team position) of the athlete in the sport;
tactics;
learning of specific technical sport's fundamentals; and
specific motor control/learning aspects (biomechanics, abilities etc. . . . )

The pre-decision-making order and the sport's specific displacement (for example with reference to FIG. 23 the full body sprint movement with a soccer ball to a specific zone in the field) is called visual-cognitive/multisensory decision-making loop. The data obtained from master/slave interfaces is used in performance calculations.

After the athlete has performed the sport's specific displacement action (full body movement), the athlete arrives within the detection zone of a cognitive slave-interface. The cognitive slave interface can vary depending on the sport, the role of the athlete, and the specific sport action being assessed or trained for. Examples are illustrated in FIG. 2B for soccer, 3B/13D for American football, and 13C for hockey. Irrespective of good or bad decision-making (displacement to the appropriate cognitive slave-interface), the cognitive slave-interface detecting the athlete's presence displays a skill order (with cognitive/multisensory stimuli) in the appropriate context of the sport, role and action being trained for. This includes a chronometric indication FIGS. 2B/13C, statistics, below/above a single threshold, a response mapping such as illustrated in FIG. 6A, etc.

The athlete has to integrate the skill order in the context of the sport to produce an expected action in the corresponding context, for example shooting to a basketball panel. For example the expected sport action can be configured in accordance with:
the targeted sport;
the role (team position) of the athlete within the sport;
tactics;
learning of specific technical sport's fundaments (shooting/passing to a target etc. . . . ); and
Specific motor control/learning aspects (biomechanics, abilities etc. . . . )

The portion including the sport skill order and the sport action is called the motor control/learning loop. The data obtained from master/slave interfaces is used for performance calculations.

The invention is not limited to the reaction-time loops described hereinabove, the cognitive-multisensory stimulation system can be configured to enforce and evaluate other reaction-time loops depending for example on the sport, the role of the athlete within a team, the sport action drill, etc. One such example is a physical reaction-time loop which concerns athlete's ability to reposition him/her-self within the play (get to a defensive/offensive position, return to the back of the tennis court after a volley, etc.) Again, The data obtained from appropriate master/slave interfaces is used for performance calculations.

The evaluation/profiling/training programs in accordance with the proposed solution include a succession of cognitive/multisensory reaction-time loops, visual-cognitive decision-making loops and motor control/learning loops that have to be performed within a best speed-accuracy trade-off. Relative to the program chosen by the coach the different loops are randomly displayed to the subject in order to obtain the data necessary for performance calculations.

The proposed cognitive-multisensory stimulation system is configured to be adapted for the specificity of a given sport by positioning the master-interface and appropriate sport relevant slave-interfaces in appropriate sport relevant positions. Moreover, the visual-cognitive decision-making loops and motor control/learning loops can be set to realistically conform to the specific cognitive and sensory-motor constraints imposed by the sport trained for. A desired performance profile in the form of a peripheral visual filed performance mapping is input, selected or determined from multiple selected athletes/subjects. Alternatively, an athlete can challenge him/her-self by adjusting general or specific thresholds against which the performance is mapped.

The performance calculations result in obtaining a current peripheral visual field mapped assessment/performance profile, one example of which is illustrated in FIG. 6A.

In general, the proposed solution objectively evaluates and trains decision-making processes by cognitively stimulating a tested subject in real sports/job action via different cognitive/multi sensory interfaces. The proposed solution provides an objective evaluation and training of motor/control learning of specific fundaments within a real sport/job. The objective profiles enable an objective ranking of athletes free of subjective indicators. With the combination of different performance data obtained at different levels of evaluation in accordance with the proposed solution, it is possible to extract an athlete's performance profile free of subjective indicators and to recommend a specific objective program to optimize the extracted profile.

Objective performance improvement is suggested by optimizing the measured profile, for example the randomization of cognitive/multisensory stimulation is biased towards attaining a more uniform performance profile output representation and eventually an optimized profile having a higher density representation towards one for example illustrated in FIG. 6B. For certainty, the invention is not limited to the profile representation illustrated in FIGS. 6A and 6B, the representation of the profile can take different visually representative forms along a variety of multidimensional parameters.

In accordance with the proposed solution, cognitive multisensory stimulations can be isolated, paired or grouped relative to the complexity of scenario to be induced. The combination of specific cognitive-multi sensory stimulation leads to corresponding specific reaction/response from athletes/subjects. The isolated, paired or grouped perceptual-cognitive stimulations correspond to low or high level perceptual-cognitive-motor processes in the brain. To provide a large range of brain processing difficulty levels, the proposed solution can use stimuli from different cultural or environment frames of reference to increase the difficulty of a task. The proposed cognitive-multisensory stimulation system evaluates the visual mapping of human cognitive-multisensory-motor reaction-time (production of a motor-reaction-time after the integration, by the brain, of different sensory and cognitive input) in live sports/job situations. The proposed solution can also evaluate tactile-motor-reaction-time and auditory-motor-reaction-time which could be useful for athletes or other populations.

Beyond these perceptual-cognitive-motor and visual aspects, the proposed system can also evaluate decision-making performance with respect to a sport/job situation requiring the best speed-accuracy trade-off (taking the best decision in the minimal time frame without producing errors) within the chronometric context of real sport/job actions and relative to the complexity of visual and cognitive loading.

For certainty, cognitive-multisensory stimulation methods and apparatus of the proposed solution can be configured for use in retaining or continuing training in injured athletes. In this regard motor-reaction-time loops can be given a lower weighting when physical displacement is involved or replaced with other limb motion. The physical recovery program can be employed in selecting the range of motions and thresholds adjusted appropriately to improve/regain injured function while the cognitive acuity involved in the cognitive/multisensory reaction-time loops and visual-cognitive decision-making loops is maintained or developed further.

In the science of sports concussions, there is a lack of objective cognitive measurable base levels which directly correlate with the reality experienced by an athlete on the field. There is also a lack of protocols and devices allowing the measurement of cognitive recovery after concussion trauma that can simulate the reality experienced by the athlete on the field. Existing concussion assessments do not take into account the complexity and the subtlety of cognitive processes experienced by the athlete during the real game. In accordance with another aspect of the proposed solution there is provided an interactive apparatus for assessing cognitive-motor performance of athletes after a disruptive incident, for example possibly suffering from concussion. Some embodiments can provide a baseline evaluation that could be used as a differential-based assessment in determining whether a given subject is exposed to a Mild Traumatic Brain Injury (MTBI). A comparison between an initial baseline assessment and a post-incident baseline assessment can lead to a clinical diagnosis of a post-traumatic concussion. Beyond this evaluation stage, some embodiments can propose a post-concussion rehabilitation program to get back to the level assessed during the initial baseline evaluation.

To reach that goal, some embodiments can be organized and configured to assess the cognitive processes which can be affected by a concussion. For example, decision-making, reaction-time and the capability to process simple or complex sensory stimulation (including unimodal, bimodal and/or multimodal stimulation in performing specific motor tasks) can be evaluated during initial baseline profiling and after the occurrence of an incident (concussion). These evaluations can be done in static or dynamic set-up relative to the capability of the athlete to perform a given task after the incident (brain trauma). This procedure allows the objective quantification of the negative impact of concussions on cognitive processes which have a major role in sports. For example, it is largely documented that concussions can disrupt reaction-time efficiency. Some embodiments compare the pre- and post-concussion baseline profiles to identify consequences of such a concussion on specific cognitive processes (reaction-time is the capability to process a sensory information and to produce an action consecutively to the sensory stimulation). This type of evaluation can be done for all the pertinent cognitive parameters that are important in sports and in human behavior (anticipation, visual memory, decision-making, visual-field detection etc.) If the concussion is asserted, some embodiments can propose a training program to progressively get back to the cognitive values obtained during the initial baseline. Then, the post-concussion baseline profile can be optimized like the athletic performance protocols described hereinabove.

In accordance with the proposed solution, the apparatus and methods generate stimuli, and preferably provide a learning and training environment, which exposes an athlete to a cognitive-multisensory overload via sensory and/or perceptual stimulation. Without limiting the invention, the sensory and/or perceptual stimulation includes: unimodal, bimodal and/or multimodal stimulation in performing specific motor tasks.

In accordance with the embodiment of the proposed solution an initial baseline profile is extracted via a calculation employing multilevel parameters (including, but not limited to: cognitive aspects, visual aspects, motor aspects. etc.) specific and relevant to a given task or field of expertise. For example, measured/detected responses, and measured response times, to a battery of stimuli can be weighted and mapped. The cognitive-multisensory stimulation system then proposes a training protocol taking into account parameters inherent to specific tasks a particular subject is involved in. For example, the training protocol can be based on a calculation which casts mapped values in the baseline profile into mapped values of a training regimen, without limiting the invention casting the mapped values can include applying weighting factors, applying transform functions, ignoring, etc. the mapped values.

Further, with appropriate changes the cognitive-multisensory stimulation system can also be used in training handicapped persons whether or athletic performance or otherwise or severe trauma patients during relearning and recovery. In this regard, presence, tactile and trigger slave interfaces can be configured detect appropriate responses. Of worthy note, special sensory stimulation slave interfaces which besides being preferably wireless can also be implants. For example, a hearing handicapped athlete/subject can employ a special auditory stimulator interfaced with the cognitive-multisensory stimulation system of the proposed solution. A dental implant can be configured as a tactile slave interface for example for rehabilitation and relearning purposes. An eye muscle tension sensor as part of a slave sensory interface can be employed in severe neck trauma recovery training.

For purposes of cognitive-multisensory stimulation assessment, profiling and training for rehabilitation, and perhaps relearning (irrespective of handicap needs) the cognitive-multisensory stimulation system can be implemented as coded logic into a combination of video game/virtual reality game hardware. Without limiting the invention thereto, currently game consoles such as Wii™, by Nintendo, Kinect™, by Microsoft, and others can be coded in accordance with the proposed solution to provide a compact, portable and personal cognitive-multisensory stimulation system for use off court, off rink, off playfield, in the office, etc. to relearn, maintain or train at least specific aspects of performance. That is, the features of aspect and configuration of the cognitive/multisensory stimulation interfaces illustrated in the figures are not required, in particular it is not required that the master interface have physical arms, for example the upper section of the master interface can be implemented as a projected display.

The cognitive-multisensory stimulation system according to the proposed solution is can be configured to create an extended interactive environment in which multiple interactive interfaces interact with each other and with the athlete/subject. For certainty, while extensive reference has been made to visual, auditory and tactile senses, stimulation and stimulators therefor, it is understood that the cognitive-multisensory stimulation system can include other type of stimulators and can provide stimuli in respect of other senses such as, but not limited to, olfactory (smell) and taste. For example, coffee or tea inspectors can benefit from training specific to their roles with an appropriate change in the cognitive-multisensory stimulation system. Being understood that the human olfactory and taste senses are less acute than perhaps in dogs and other animals, with an appropriate change in shape and size, the proposed solution can be configured for animal training, such as but not limited to: eye seeing dogs, police dogs, medical companion dogs, explosives sniffer pigs, etc. Taste stimulators can include canulae, dental implants or dental appliances. Smell stimulators themselves can have various forms to resemble actual objects as teaching working animals to make an abstraction with respect to the source of such stimulus may detract from the intended training.

While the proposed solution has been described with respect to the master-interface and slave-interfaces illustrated in the figures, it is understood that such master and slave interfaces represent only examples and in no way limit the invention thereto. One of the aspects of the proposed solution is to provide a cognitive-multisensory stimulation system which replicates real life sports action and job situations. In this regard, components such, as but not limited to, the slave cognitive interfaces can be implemented into virtual team player standees for example as illustrated in FIG. 2B for soccer and the post-shaped cognitive interfaces illustrated in FIGS. 13C, 18 and 21 can be implemented into the protective glass frame of the hockey rink. The vibratory slave interface can also be integrated into a bat, stick, racket handle, bow handle, etc. Additionally, master interface is not limited to the features of shape and configuration illustrated in the FIG. 1. The master interface can be implemented as a fixed projected screen instead of the radial arms and LCD display hub. As well the master interface can be implemented as a display moving with the athlete/subject. Such a moving display includes two types a wearable display, such as a head mounted display or a retinal projection display, and a virtual reality display. One example of such a virtual reality display can be implemented using the advertising projecting equipment typically employed in sports arenas which project directly on the ice rink or basketball court for example. The virtual reality display can be configured to follow the athlete/subject during the displacement tasks for example, much like a head-up display. With such a virtual reality master interface, the baseline position itself can be randomly positioned as a projected marker. Pucks, balls, hockey sticks, bats, rackets, paddles, pedals, arrows, foot ware, sports specific clothing, etc. can include infra-red reflective markers wherein presence, trip and trigger slave interfaces can be implemented as an infra-red camera system tracking the infra-red markers within the field, court, rink, etc. thus further enhancing the real life sports environment without hindering full body movement. With respect to stimulating the peripheral vision of the athlete/subject the invention is not limited to using a master cognitive interface described exclusively. For example sports arenas typically employ an advertising band along the front of balconies, this advertising band during practice can be employed to provide peripheral vision cues and/or to ensure that the athlete's gaze is properly oriented during pre-stimulation and/or stimulation.

In accordance with the proposed solution, advantages are derived from performance training employing high order complex cognitive processing in evaluating and improving performance by imposing a different level of decision-making complexity for subjects in real life situations by imposing low-levels and high-levels of cognitive loading.

The solution proposed herein enables a large spectrum of stimulation in different sensory modalities which include visual, auditory, tactile and other senses. In the general context "sensory signal" means a visual, haptic, vibratory, audio, or any other suitable stimulation of the human senses.

While extensive references have been made to athletic performance, the invention is not limited thereto. "Athlete" means a person performing a physical task requiring concentration and responsiveness to his or her surroundings. "Athletic performance" means the performance activity of an athlete. With appropriate modifications, the proposed solution can be implemented in a variety of disciplines, professions and/or situations including but not limited to: military training, astronaut training, etc. where an ultra-rapid response is valued and/or necessary. Therefore in the greater sense a subject can include, but is not limited to: a professional or amateur sports player, a soldier, a firefighter, a police officer, a scuba diver, etc.

While the invention has been shown and described with referenced to preferred embodiments thereof, it will be recognized by those skilled in the art that various changes in form and detail may be made therein without departing from the spirit and scope of the invention as defined by the appended claims.

What is claimed is:

1. A method of assessing a cerebral disruptive incident comprising:
   obtaining a baseline cognitive performance profile at a first point in time prior to said disruptive incident;
   storing said baseline cognitive performance profile;
   obtaining a secondary cognitive performance profile following said disruptive incident; and
   comparing said baseline cognitive performance profile with said second cognitive performance profile to determine a measure of cognitive impairment due to said disruptive incident, wherein said obtaining said baseline cognitive performance profile and said obtaining said secondary cognitive performance profile comprise:
      establishing with a patient a sensory semantic language for relating a plurality of symbols, wherein each symbol has a meaning that is unknown to the patient prior to said establishment of said sensory semantic language, to a plurality of affirmative actions requiring that the patient do something, wherein each action of said plurality of affirmative actions is associated, based on said sensory semantic language, with a symbol of said plurality of symbols, said sensory semantic language being new to said patient prior to said establishment;
      instructing said patient to perform a cognitive exercise, wherein, during said exercise, said patient is provided in a central field of view of said patient a selected one of said plurality of symbols;
      driving a transducer for generating a luminous output for providing at least one peripheral visual stimulus located in a peripheral vision region of the patient, said luminous output generated a period after said providing said selected one of said plurality of symbols;
      detecting a responsive affirmative action performed by said patient after said generating said luminous output; and
      determining if said responsive affirmative action is accurate based on said selected one of said plurality of symbols provided in said central field of view of said patient and said established sensory semantic language.

2. The method as claimed in claim 1, wherein said processing said decision making data comprises measuring a response time to said at least one peripheral visual stimulus as a function of peripheral vision location of said at least one peripheral visual stimulus to provide data representing a response time map over peripheral vision location.

3. A system for assessing a cerebral disruptive incident comprising:
   a computerized interactive system for obtaining a baseline cognitive performance profile comprising:
      at least one cognitive human-machine interface for providing a selected one of a plurality of symbols in a central field of view of a patient, and for providing one or more peripheral visual stimuli located in a peripheral vision region of the patient, comprising a processing unit executing machine logic instructions providing said one or more peripheral visual stimuli during an exercise a period of time after said providing a selected one of a plurality of symbols; and
      a controller configured to:
         instruct said at least one cognitive human-interface to present to said patient, at a given time, a selected one of said plurality of symbols, wherein a sensory semantic language is stored in memory of said controller that relates each action of a plurality of actions, wherein for each action of said plurality of actions the patient is required to do something, to one or more symbols of said plurality of symbols, and wherein each symbol of said plurality of symbols has a meaning that is unknown to the patient prior to establishing said sensory semantic language with said patient;
         calculate the time from said provision of said one or more peripheral visual stimuli to said provision of a response by the patient to said selected one of said plurality of symbols as an action performed by the patient, said controller including a central processing unit executing machine logic instructions determining whether the patient correctly responds to said selected symbol, wherein said sensory semantic language is processed by said controller for said determining to verify if said provision of said response is accurate as a function of said sensory semantic language and said selected one of said visually-presented symbols;
      a baseline profile storage unit configured to store said baseline cognitive performance profile;
      a comparing unit configured to compare said baseline cognitive performance profile obtained at a point in time prior to said disruptive incident with a secondary cognitive performance profile obtained at a point in time following the disruptive incident to determine a measure of cognitive impairment due to said disruptive incident.

4. The system as claimed in claim 3, wherein said controller is further configured to measure a response time to said selected one of said plurality of symbols as a function of peripheral vision location of said at least one peripheral visual stimulus to provide data representing a response time map over peripheral vision location.

* * * * *